United States Patent [19]

Krawetz et al.

[11] Patent Number: 4,758,408
[45] Date of Patent: Jul. 19, 1988

[54] AUTOMATIC OXYGEN MEASURING SYSTEM

[75] Inventors: Arthur A. Krawetz, Evanston; Theodore Tovrog, Mt Prospect, both of Ill.

[73] Assignee: The United States of America as represented by the Secretary of the Air Force, Washington, D.C.

[21] Appl. No.: 705,950

[22] Filed: Feb. 27, 1985

[51] Int. Cl.$^4$ ............................................. G01N 7/02
[52] U.S. Cl. .......................................... 422/92; 73/19; 422/83; 436/148
[58] Field of Search ................... 422/83, 88, 92, 79; 436/62, 75, 138, 148, 180, 181

[56] References Cited

U.S. PATENT DOCUMENTS

| | | | |
|---|---|---|---|
| 1,374,391 | 4/1921 | Rodhe | 422/83 |
| 2,987,912 | 6/1961 | Jacobson | 73/19 |
| 3,740,320 | 6/1973 | Arthur | 195/102.5 R |
| 4,148,612 | 4/1979 | Taylor et al. | 422/83 |
| 4,365,505 | 12/1982 | Holzl | 73/19 |
| 4,395,902 | 8/1983 | Espenscheid et al. | 73/19 |

FOREIGN PATENT DOCUMENTS

| | | | |
|---|---|---|---|
| 118114 | 8/1919 | United Kingdom | 422/83 |
| 1377044 | 12/1974 | United Kingdom | 422/79 |

OTHER PUBLICATIONS

A. A. Krawetz, et al., Chemical and Physical Properties of Lubricants and Hydraulic Fluids, AFML-TR-76-166, Air Force Materials Laboratory, Air Force Wright Aeronautical Laboratories, Air Force Systems Command, WPAFB, OH 45433.

Primary Examiner—Michael S. Marcus
Attorney, Agent, or Firm—Stanton E. Collier; Donald J. Singer

[57] ABSTRACT

An automatic oxygen absorption measuring system has a controllable source of pressurized oxygen, a controllable venting device, and a device for indicating incremental gas volume changes connected through a controlled gas reservoir to an oxygen circulating testing section where oxygen is passed through a liquid sample at a fixed temperature. Upon the liberation of other gases than oxygen or absorption of oxygen, the gas pressure changes a liquid fluid level in the device for indicating incremental gas changes. An electronic circuit causes the venting or inputting of gas until an equilibrium pressure is obtained. Each change is noted on a recording device. The device for indicating incremental gas volume changes has two glass bulbs attached in line with a manometer filled with electrically conductive liquid fluid. Four electrical contacts placed about the bulbs indicate the level of the liquid fluid. In response to the liquid contacting these contacts, the electronic circuit operates the controllable devices to achieve an equilibrium pressure.

6 Claims, 4 Drawing Sheets

AUTOMATIC OXYGEN MEASURING SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to an automated measuring system for determining gas contents of fluids, and, in particular, relates to a system for determining the inherent oxidation stability of base oils and lubricants over a temperature range and for a period of time.

A great variety of standardized tests have been developed over the years in an attempt to simulate in the laboratory the conditions of oxidation to which lubricants are exposed during the course of their operative life. These have been used for the evaluation of finished oils, base stocks, additive packages and the catalytic effects of various elements, compounds and metal alloys. In general the test procedures may be categorized into two groups.

In the first group oxidation is measured by virtue of changes in the properties of the sample lubricant subjected to oxidative stress. Thus in that case measurements of changes in acidity, viscosity, sediment formation, infrared absorption, additive depletion, color corrosibility or dissolved metal content might be used as an index of the state of sample degradation produced by oxidative stress.

Examples of oxidation tests of the first type may be found in Federal Test Method Standard 791b, Method 5307, Corrosiveness and Oxidation-Stability of Aircfaft Turbine Engine Lubricants and Method 5308.6 Corrosiveness and Oxidation Stability of Light Oils. Other related standard tests of the same general type include Institute of Petroleum Standard IP 280, Oxidation Stability of Inhibited Mineral Turbine Oils, American Society for Testing and Materials Standards, ASTM D 2893, Standard Method of Test for the Oxidation Characteristics of Extreme Pressure Oils, ASTM D 943, Standard Method of Test for the Oxidation Characteristics of Inhibited Steam Turbine Oils, ASTM D 1313, Standard Method of Test for Sludge Formation by High Pressure Oxidation Bomb, and ASTM D 873, Standard Method of Test for Oxidation Stability of Aviation Fuels (Potential Residue Method). Industrial standards such as the International Harvester BT-10 oxidation test have achieved a wide degree of acceptance. The aforementioned list contains representative members of the first class of oxidation tests.

A secondly widely applied class of oxidation tests exists in which oxygen absorption by the sample is measured directly as an index of the chemical strain produced by oxidative stress. Examples of this category are as follows: American Society for Testing and Materials tests ASTM D 2272, Standard Method of Test of Continuity of Steam-Turbine Oil Oxidation Stability by Rotating Bomb, ASTM D 1402, Standard Method of Test for the Effect of Copper on Oxidation Rate of Grease, ASTM D 525, Oxidation Stability of Gasoline (Induction Period Method) and D 942, Standard Method of Test for the Oxidation Stability of Lubricating Greases by the Oxygen Bomb Method.

In all of the above group of tests oxygen in contact with the sample at elevated pressure and temperature is consumed by reaction with the sample and the amount of such consumption determined by measurement of a decrease in oxygen pressure. With the exception of the rotating bomb method, each of the tests involves static oxygen under pressure in contact with an essentially immobile sample interface. The contact surface to sample volume ratio is at a minimum. Because of this and because reaction products accumulate at the surface, measured induction periods are increased and reactions tend to be shut off by virtue of a blanket of reaction products between the sample and the source of oxygen. A manual system as shown in FIG. 1 is used in the past to accomplish oxidative analysis has therein the following items: An oxygen supply connected through a first valve shown as $S_1$ to a second valve shown as $S_2$. The second valve is connected to a third valve and a fifth valve. The third valve is further separately connected to a manometer and a gas buret with a leveling bottle thereon. The manometer is further connected to a compensator tube through a fourth valve. The fifth valve is connected to a ninth valve, an eight valve, and a gas reservoir. The gas reservoir is further connected to a sixth valve. The sixth valve is connected to a gas pump and to a vacuum gauge separately. The vacuum gauge is connected through a seventh valve to a vacuum pump. The gas pump is further connected to the eight valve located in the bypass line and a tenth valve. The tenth valve is connected to a flowmeter having thereafter in a flow path a liquid trap. The liquid trap is connected to a reaction section after passing through a water condenser. From the reaction section the flow passes through the water condenser connected thereabout and into an ambient temperature trap, a cold trap, an ascarite trap, an anhydrone trap and a molecular sieve trap. The molecular sieve trap is connected to the ninth valve which is connected to both the fifth valve and the bypass line with the eight valve therein. Once test conditions are established, a continuous flow path is set up through the following items in the manual system in order: the gas reservoir, the sixth valve, the gas pump, the tenth valve, the flow meter, the liquid trap, the water condenser, the reaction section, the water condenser, the ambient temperature trap, the cold trap, the ascarite trap, the anhydrone trap, the molecular sieve, the ninth valve and the fifth valve. Gas also flows from the gas pump through the bypass line with the eight valve therein.

After the system has been purged, pressure established and temperature stabilized, the gas volume change is measured at predetermined intervals as follows: turn off the gas circulating pump; turn the second, third, and fifth valves to join the gas reservoir to the gas buret, equalize the mercury levels in the buret and the leveling bulb, turn the third valve to the manometer and note imbalance, if any. If there is an imbalance, turn third valve to the gas reservoir and adjust the leveling bulb in a manner to correct the imbalance; turn the third valve to the manometer and recheck the pressure; repeat the last two steps as required to bring the manometer in balance; immediately turn the fifth valve to the circulate mode and restart the gas pump; and finally record the new buret volume and temperature. This manual procedure is repeated for each time interval. One clearly sees that for a long test run involving two dozen checks or more that this manual apparatus is very time consuming and subject to error.

SUMMARY OF THE INVENTION

The instant invention sets forth an automatic oxygen absorption measuring system and thereby overcomes the problems set forth hereinabove.

In the present invention, a source of oxygen enters through a pressure regulator with a low pressure valve therein to a surge space having thereon a first solenoid valve in a normally closed (NC) position. The first valve (NC) is connected to a second solenoid valve (NC) for venting, to a third valve for a modified gas buret, to a fourth valve normally open (NO) for controlling a gas reservoir, and to a liquid fluid movement indicating device responsive to changes in gas pressure in a gas reservoir. A manometer is openly connected between the liquid fluid movement indicating device, a leveling bulb with a sixth valve thereon, and the gas buret.

The fourth valve (NO), in addition to the above, is connected to a gas reservoir which is further connected to a fifth valve (NO) being time delay controlled. A pressure gauge is connected between the fifth valve (NO) and a seventh valve.

When operating, gas flows through the following items: a gas pump, a gas reservoir, a flow control valve, a flowmeter, a liquid/particle trap, a water condenser, a reaction section, the water condenser, an ambient temperature trap, a cold trap, absorbers, two stopcock valves in series with a purge valve therebetween, and the seventh valve to the gas pump. A bypass line with a ninth valve is connected after the gas pump and after the stopcock valves in the above flow sequence.

The liquid fluid movement indicating device has an upper and a lower volume bulb in series with the manometer. An electrically conducting fluid moves therein in response to pressure changes in the gas reservoir. The conductive fluid can establish electrically conductive paths between a first, a second, a third, and a fourth electrical contact placed in the flow path. The fourth contact is common at all times to the liquid fluid. The second contact is directly below the lower bulb, the first contact is between the upper and lower bulb, and the third contact is directly above the upper bulb. Depending upon the contacts touched by the liquid fluid, the actuator valves and recorders react in response thereto to record changes in volume. The electronic devices for automatically recording changes in gas volume in response to the movement of the conductive fluid are as follows: two controllers, four relays, a strip chart recorder or a computer with an interface device; four solenoid valves: the first, second, fourth, and fifth valves mentioned hereinabove; a volt divider, and power sources both dc and ac.

One object of the present invention is an automatic gas absorption measuring system.

Another object of the present invention is a gas volume change device that measures incremental changes in volume.

A further object of the present invention is the necessary electronic means for automating the recording of gas volume changes.

These and many other objects and advantages of the present invention will be readily apparent to one skilled in the pertinent art from the following detailed description of a preferred embodiment of the invention and the related drawings.

BRIEF DESCRIPTION OF THE DRAWINGS

FIG. 5 is a graph of oxygen absorption;

FIG. 6 is a graph of oxygen absorption rate; and

FIG. 7 is a graph of total oxygen absorption.

DETAILED DESCRIPTION OF THE PREFERRED EMBODIMENT

Figure 1:
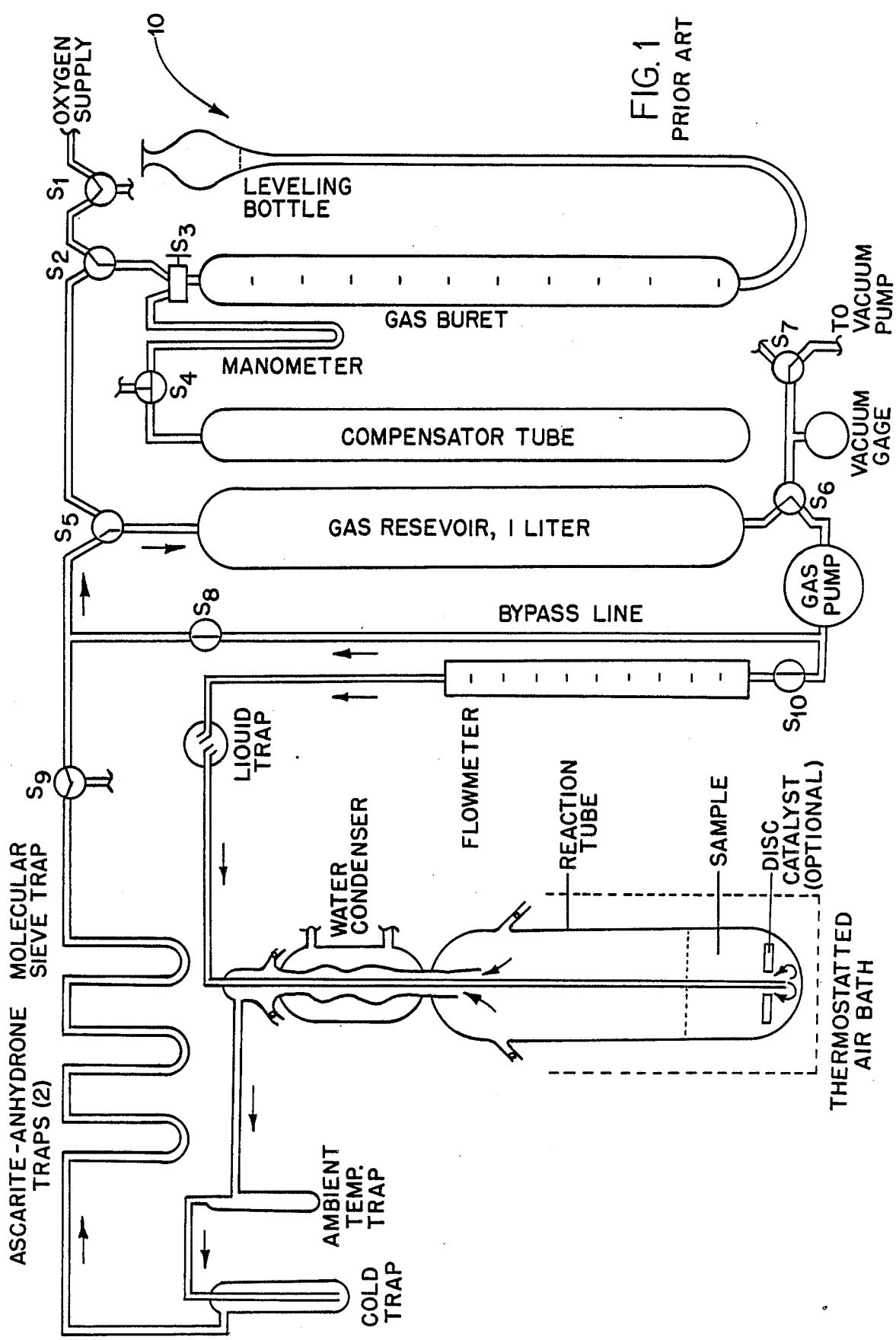
FIG. 1 is a schematic of the prior manually operated oxygen absorption measuring system.
Figure 2:
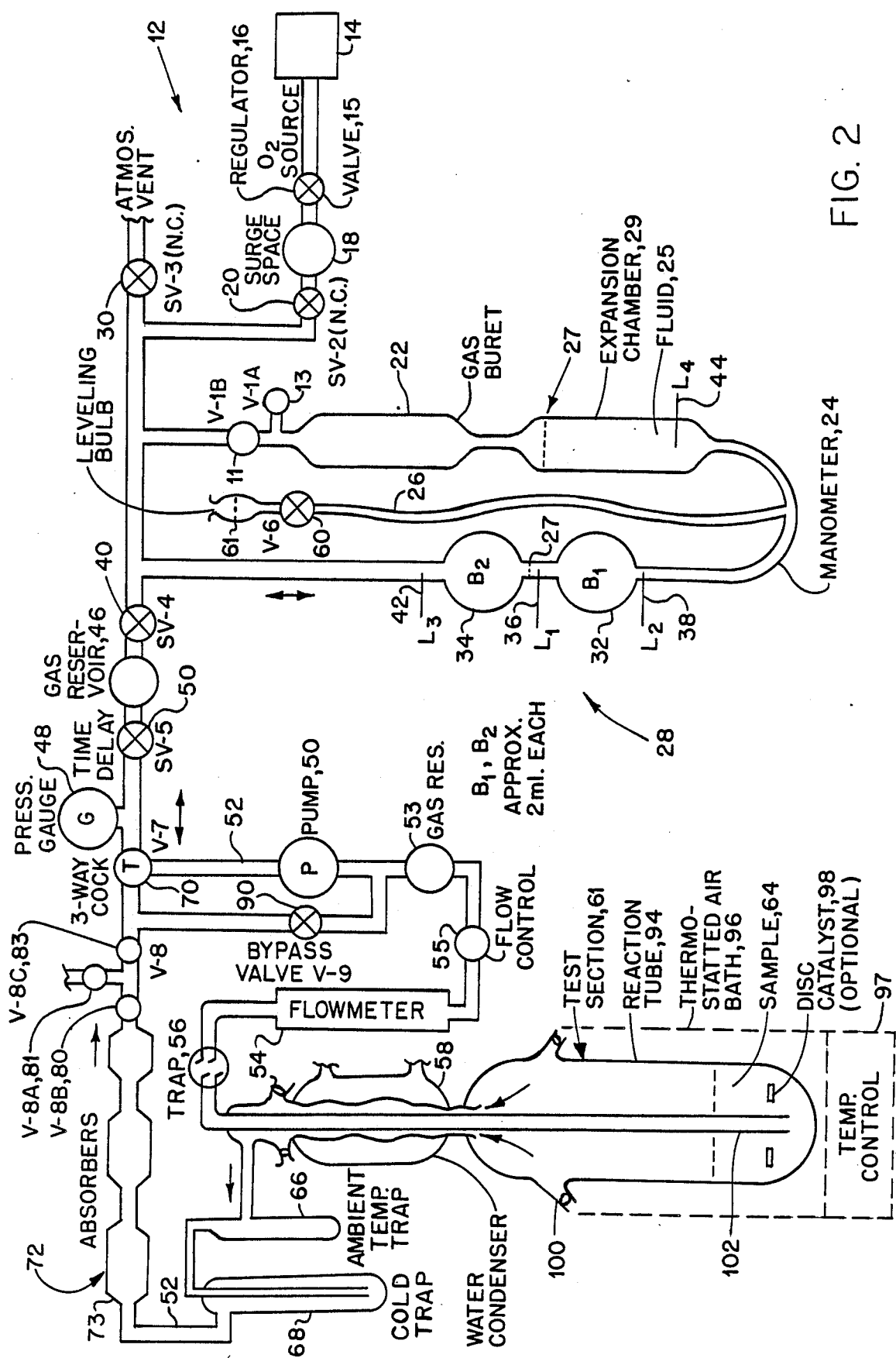
FIG. 2 is a schematic of the present invention oxygen absorption measuring system.

Referring to FIG. 1, a prior manual oxygen absorption system 10 is shown. The automatic oxygen absorption measuring system 12 of the present invention is shown in FIG. 2.

Apparatus 12 has an oxygen source 14 whose output pressure is controlled by a pressure regulator 16. A low pressure valve is an integral part of gas regulator 16. A surge space 18 connected thereto absorbs any rapid pressure changes. The entrance of oxygen to system 12 is controlled by a solenoid valve 20, normally closed, and noted as SV-2 on FIG. 2 and in FIG. 3. These items are noted as item 200 in the drawings and the group is noted as the controllable source of gas pressure. A solenoid valve 30 also noted as being a controllable means for relieving excess pressure, SV-3, normally closed (NC), can be opened to allow excess pressure in system 12 to be vented during automatic operation.

Initial preparation such as system purging and liquid level adjusting is obtained by means of two stopcocks 11 and 13, V-1B and V-1A, respectively, a gas buret 22, a manometer 24 filled with an electrical conductive fluid like mercury, and a leveling bulb 26 with a valve 60, V-6, thereon.

A further procedure to follow is the check for leaks. The following steps are performed: (1) turning on power; (2) adjusting regulator 16 to deliver approximately 6 psig; (3) opening valves 13, V-1A; 11, V-1B; 81, V-8A; 80, V-8B; and 83, V-8C; (4) closing valve 60, V-6, if open, and raising leveling bulb 26 so the mercury level 61 is approximately 15 cm. above a contact 36, $L_1$, in volume change device 28; (5) partially opening valve 60, V-6, and allowing the mercury level 27 in an expansion chamber 29 above a contact 44, $L_4$, to rise slightly above a contact 42, $L_3$ (mercury will also rise from contact 36, $L_1$, to slightly above contact 42, $L_3$); (6) closing valve 60, V-6; (7) closing valves 13, 11, 81; V-1A, 1-1B, and V-8A respectively; (8) partially opening low pressure delivery valve 15 on regulator 16 depressing the mercury from contact 42 to 36, $L_3$ to $L_1$; (9) adjusting the oxygen input valve 20 to reduce pressure and minimize overshooting contact 36, $L_1$; (10) starting computer; (11) allowing system 12 to run for a sufficient time to check for leaks, (12) closing low pressure delivery valve 15 on regulator 16; (13) opening valves 13 and 81, V-1A and V-8A respectively; (14) adjusting leveling bulb 26 with valve 60, V-6, open to allow contact to be made between mercury fluid 25 and contact 36, $L_1$; (15), closing valve 60, V-6; and (16) stopping the computer.

Once system 12 is purged and leak checked, a fluid level 27 is adjusted in volume change device 28 also noted, in general, as item 202 in the drawings and also called means for indicating incremental gas volume changes, having a lower bulb 32 and an upper bulb 34, both having a volume of about 2 milliliters, with electrical contacts 36, $L_1$; 38, $L_2$; 42, $L_3$; and 44, $L_4$. Initial, mercury fluid 25 is placed slightly over contact 36, $L_1$, which is the equilibrium pressure established at the start of the run. As pressure increases, level 27 of the mercury will move past contact 38, $L_2$, and as the pressure decreases sufficiently, will move above contact 42, $L_3$. Contact 44, $L_4$, is normally always in electrical contact with mercury fluid 25 and this acts as an electrical common. Depending on the contacts engaged, system 12 will act accordingly as to be described in the operating procedures.

Although system 12 uses an electrically conductive fluid 25 to establish electrical paths between contacts 44, 42, 38 and 36, another equally effective means for monitoring fluid movement can be electro-optic switches that are switched by breaking a light beam across the flow path.

A solenoid valve 40, SV-4, and a solenoid valve 50, SV-5, are placed in series about a gas resevoir 46 also shown as item 206 in FIG. 2 being referred to as means for controlling said gas reservoir. A pressure gauge 48 is used initially to monitor the gas pressure in system 12. A 3-way cock 70 is attached after pressure gauge 48 and in a gas circulation line 52 between a stopcock valve 83, V-8C, and a gas pump 50. A bypass valve 90 is placed in a line between the output line of the gas pump 50 and the output line of stop cock valve 83. A flow control valve 55 is used to adjust the gas flow volume in gas circulation line 52. A flowmeter 54 is connected after valve 55 in line 52.

Following flowmeter 54 and in order are the following items: a trap 56, a test section 61 with a reaction tube 94 with a liquid test sample 64 therein with a temperature control 97, a water condenser 58, an ambient temperature trap 66, a cold trap 68, absorbers 72, stopcocks 80 and 83, 3-way cock 70, and pump 50.

Figure 3:
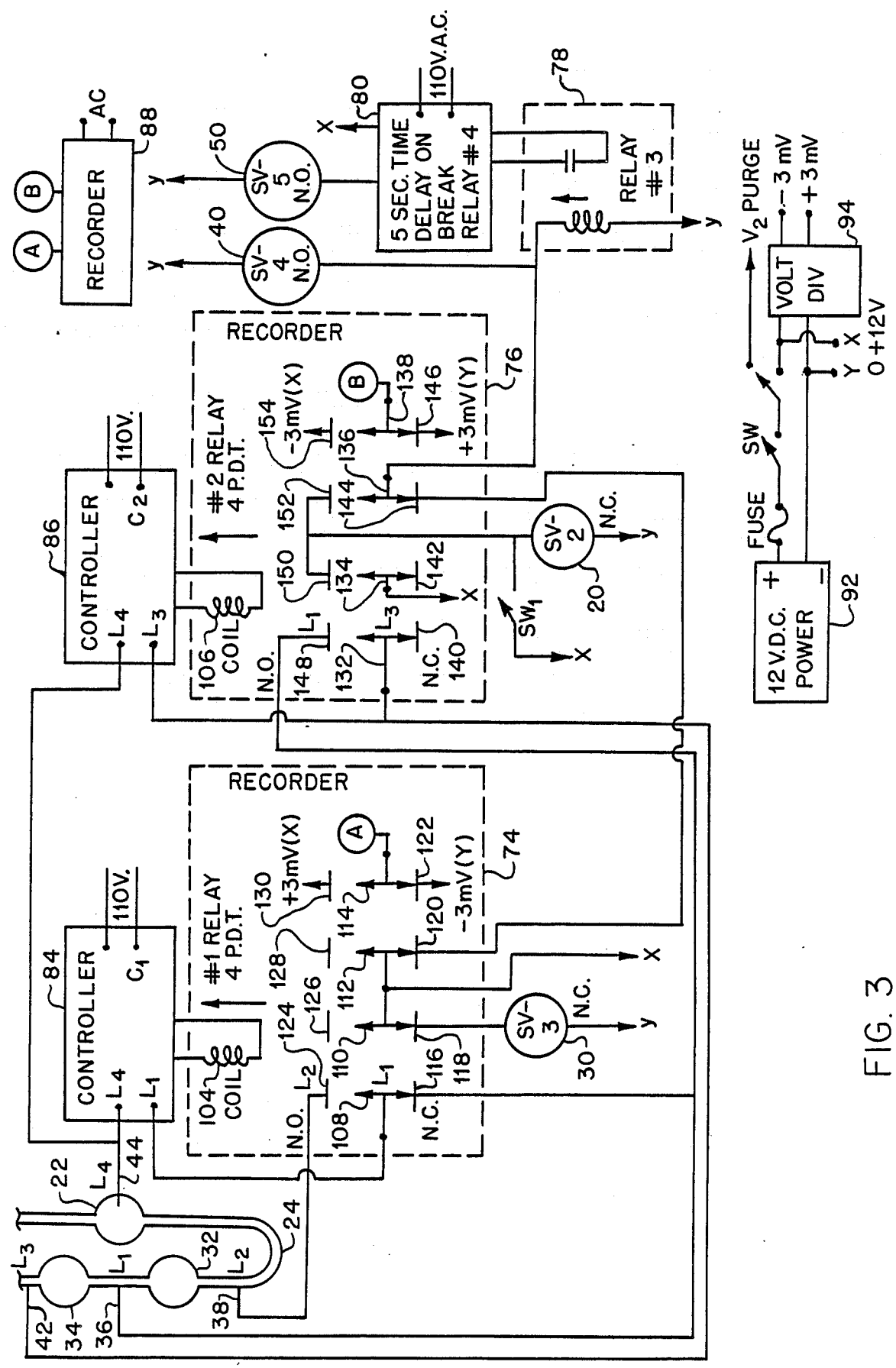
FIG. 3 is an electrical schematic of the electronics required to automate the system of FIG. 2.

The electrical schematic for automatic oxygen absorption measuring system 12 is shown in FIG. 3. The devices used in the schematic are as follows:

| ITEM | MODEL |
|---|---|
| Relay 74 | Sigma Relay 67RV4SCO |
| Relay 76 | Sigma Relay 67RV4SCO |
| Relay 78 | Potter & Brumfeld KVP11D55 |
| Relay 82 | Struthers Dunn Time Delay 42-60 |
| Controller 84 | Cole Parmer Model 7188 |
| Controller 86 | Cole Parmer Model 7188 |
| Solenoid Valve 20 | Clippard EV-2-12 NC |
| Solenoid Valve 30 | Clippard EV-2-12 NC |
| Solenoid Valve 40 | Clippard EV-3-12 NC |
| Solenoid Valve 50 | Clippard EV-3-12 NC |
| Strip Chart Recorder 88 | |
| 12 VDC source 92 | |
| Volt Divider 94 | |

The electrical schematic of FIG. 3 outputs to strip chart recorder 88 either positive or negative pulses to indicate incremental increases or decreases in the gas volume of system 12 when operating in the unattended mode. Clearly a computer 160, shown in FIG. 4 can be put in place of recorder 88 for data recording and analysis which will be explained hereinbelow. The manner of operating electrical schematic in FIG. 3 will be explained in conjunction with the operating procedures hereinafter.

Referring to FIG. 2, an absorber 73 closest to cold trap 68 is packed half way with an $H_2O$ absorbant such as "Anhydrone." The other half is packed with a $CO_2$ absorbant such as "Ascarite."

One inserts an empty reaction tube 94, FIG. 2, in a thermostatted air bath 96, turns on bath 96 and allows it to come to equilibrium at the preselected test temperature. If a metal catalyst 98 is to be used, one polishes all surfaces as described in Federal Test Method Standard 791b, Method 5307, air drys and weighs. One then weighs a clean reaction tube 94 (without O-ring 100), adds 10 ml of sample 64 and reweighs. Catalyst disc 98 is placed, if required, at end of an air tube 102. System 12 is assembled by inserting O-ring 100 and attaching condenser 58 and air tube 102 to reaction tube 94 in such a manner that the oxygen air tube 102 passes through the center hole in catalyst disc 98. All joints are clamped and attached to system 12 by the appropriate tubing connections. Condenser coolant is turned on and cold trap 68 is packed in ice, dry ice or liquid nitrogen as required.

Temperature control 97 can be a movable furnace which is turned on and moved to a preheating position away from the reaction tube 94. A desired temperature is obtained in this position.

It should be noted that the invention may be used for the measurement of oxygen absorption from air as well as from a pure oxygen environment. If the initial purge steps are omitted and system 12 is flushed with air initially, the absorption medium will have the composition of air. Oxygen loss will be replaced by pure oxygen so that the net composition of the gaseous medium will remain unchanged—namely, if it was air to begin with, it will retain the composition of air; and if it was oxygen to begin with, it will remain as oxygen.

To purge system 12 for pure oxygen, the power being on and $O_2$ regulator 16 adjusted to deliver 6 psig, low pressure delivery valve 15 of regulator 16 is turned on. Valves 13 (V-1A) and 83 (V-8C) are closed and valves 11 (V-1B) and 81 (V-8A) are opened. Other valves in the system are adjusted during purge pumping of flowmeter 54, reaction tube 94, ambient temperature trap 66, cold trap 68 and absorbers 22. After a sufficient length of time, valves 11 (V-1B) and 81 (V-8A) are closed.

With valve 11 (V-1) open, manometer 24 fluid level 27 is adjusted so fluid 25 just touches electrical contact 36 ($L_1$). These items are noted, in general, as item 208 in FIG. 2 and called the means for initially moving said liquid fluid level. System 12 is pressurized with oxygen to 760 torr (a level which is usually slightly above ambient pressure) by manipulation of valve 20 (SV-2) and pressure regulator 16 on oxygen supply 14. Valve 20 (SV-2) is then closed. Then one must repeat two times the pressure release and pressurizing steps. Finally, valves 11 (V-1) and 60 (V-6) are closed.

Then to start a test run, valve 20 (SV-2) is closed and pump 50 is started. Valve 83 (V-8C) is slowly opened. One adjusts flow control valve 55 to give a desired gas flow. One maintains minimum restriction in pump bypass valve 90 and uses flow control valve 55 to fine adjust the flow rate. Once set, pump bypass valve 90 should not need readjustment. Once the flow is set, computer 160 is started.

An empty test tube is removed from the furnace, not shown, after temperaure equilibrium. The furnace is then placed below reaction tube 94 and the furnace is raised to the operating level. Computer 160 is instructed to start the test and will continue to monitor the test until manually stopped.

At the end of the test run, (1) one turns computer 160 off or strip chart recorder 88 off, (2) turns the furnace off and lowers it away from reaction tube 94, (3) turns off pump 50 and opens valves 13 (V-1A) and 81 (V-8A), (4) allows reaction tube 94 to cool and shuts off water condenser 58; (5) closes valves 13 (V-1A) and 91 (V-8A) and opens valve 11 (V-1B); (6) purges system 12 of the atmosphere therein for testing; 7) turns off $O_2$; opens valves 13 (V-1A) and 183 (V-8C); (8) reaction tube 94, traps 66 and 68, are all reweighed; (9) the acidity of atmosphere purge and trap contents is determined if necessary, and (10) test sample 64 is checked for viscosity, acidity, etc.

Referring to FIG. 3, a means for activating 204 includes two controllers 84 ($C_1$) and 86 ($C_2$) which are the basic control mechanism used in apparatus 12. Controller 84 ($C_1$) activates a coil 104 of a 4-pole, double throw relay 74 when continuity occurs between contacts 36 ($L_1$), 38 ($L_2$) and 44 ($L_4$) Controller 86 ($C_2$) activates a coil 106 of a second 4-pole, double throw relay 76 when continuity occurs between contacts 44 ($L_4$), 38 ($L_2$), 36 ($L_1$) and 42 ($L_3$). When controller 84 ($C_1$) activates relay 74, arms 108, 110, 112 and 114 are moved from lower contacts 116, 118, 120 and 122, respectively, to upper contacts 124, 126, 128 and 130, respectively, and when controller 86 ($C_2$) activates relay 76, arms 132, 134, 136, and 138 are moved from lower contacts 140, 142, 144, and 146, respectively to upper contacts 148, 150, 152 and 154, respectively.

Initially the equilibrium oxygen working pressure (760 torr or other desired pressure) is set with manometer 24 fluid just making contact with contact 36 ($L_1$) The common contact 44 ($L_4$) is immersed in manometer 24 fluid at all times. Under these conditions, controller 86 ($C_2$) will be in the "off" condition because there is no contact between contact 42 ($L_3$) and contact 44 ($L_4$) Oxygen valve 20 (SV-2) will then be in its normally closed state because arm 134 is not touching upon contact 150. Controller 84 ($C_1$) will be in the "on" condition because electrical contact exists between contacts 36 ($L_1$) and 44 ($L_4$) Coil 104 of relay 74 (R1) will be activated and a "latch" contact is made between contacts 36 ($L_1$) and 38 ($L_2$) so that controller 84 ($C_1$) will remain on until manometer 24 fluid falls below contact 38 ($L_2$). Also initially, vent valve 30 (SV-3) closes and remains in the normally closed state; the time print circuit changes polarity depending on whether gas volume is increasing or decreasing and valves 40 (SV-4) and 50 (SV-5) open and remain in the normally open condition.

If the gas volume of system 12 increases (gas evolution occurs from the sample) sufficiently to produce a pressure change large enough to lower manometer 24 fluid level 27 below contact 38 ($L_2$), the following actions occur: Controller 84 ($C_1$) goes to the "off" conditions and deactivates coil 104 of relay 74 ($R_1$) As a result, the "latch" between contacts 36 ($L_1$) and 38 ($L_2$) opens, valve 30 (SV-3) vents excess pressure from system 12 (to the atmosphere or to an absorbing fluid), the time print circuit changes polarity to indicate gas evolution and valves 40 (SV-4) and 50 (SV-5) close. As pressure equilibrium is restored manometer 24 fluid level 27 rises, makes contact with contact 36 ($L_1$) and turns controller 84 ($C_1$) to the "on" condition which energizes coil 104 of relay 74 ($R_1$) causing contact 36 ($L_1$) and contact 38 ($L_2$) to go to "latch", vent valve 30 (SV-3) closes and valve 40 (SV-4) opens. If there is still excess pressure in reservoir 46 between valves 40 (SV-4) and 50 (SV-5) which is sufficient to depress manometer 24 fluid level 27 below contact 38 ($L_2$) the above process is repeated until the pressure is reduced to the desired level in a stepwise manner. If, however, the pressure in reservoir 46 is not sufficient to lower manometer 24 fluid past contact 38 ($L_2$) within 5 seconds, valve 50 (SV-5) opens and system returns to its initial equilibrium state. In the above mode of operation a recorder 88 records each stepwise elimination of excess gas as the rejection of a volume proportional to that of bulb 32 ($B_1$) in system 12. The sum of such incremental volume increases is the total of gas production which occurs during a test.

If the gas volume of system 12 decreases (oxygen is absorbed by the sample or acid gases and/or moisture are absorbed after their production by reaction with sample 64) sufficiently to produce a pressure drop large enough to raise manometer 24 fluid level 27 to contact 42 ($L_3$), the following actions occur: Controller 84 ($C_1$) will be in the "on" condition and all the conditions produced as a result thereof as noted above will occur. Controller 86 ($C_2$) will also go to an "on" condition and coil 106 of relay 76 ($R_2$) will be activated. This will cause contacts 36 ($L_1$) and 42 ($L_3$) to go to a "latched" condition in which relay 76 ($R_2$) will hold arm 132 against upper contact 148 until manometer 24 fluid level 27 subsequently falls to the level of contact 36 ($L_1$) Valves 40 (SV-4) and 50 (SV-5) which are normally open will be activated so that they close immediately. Valve 20 (SV-2) is energized and opens to admit oxygen to system 12. Finally, the time print circuit changes polarity to indicate that the predominant reaction prevailing in the system is one which results in loss of gas pressure (i.e., oxygen absorption).

As oxygen is admitted to system 12 manometer 12 fluid level drops until it reaches contact 36 ($L_1$). At that point controller 84 ($C_1$) is still in the "on" state. Controller 86 ($C_2$), however, turns "off". This action causes the latch between contacts 36 ($L_1$) and 42 ($L_3$) to break and as the current to valve 20 (SV-2) is, thus, interrupted, valve 20 (SV-2) reverts to its normally closed state. Valve 40 (SV-4) now opens. If sufficient vacuum remains in the reservoir between valves 40 (SV-4) and 50 (SV-5) to elevate manometer 24 fluid back to contact 42 ($L_3$) system 12 will again cycle to admit more oxygen. If manometer 24 fluid level 27 does not return to contact 42 ($L_3$) within five seconds, valve 50 (SV-5) opens and system 12 returns to its initial equilibrium condition. In the above mode of operation recorder 88 records each stepwise addition of oxygen as an increment of oxygen to replace an amount consumed which is proportional in volume to that of bulb 34 ($B_2$) The sum of such volumes is the total of oxygen absorption which occurs during a test. In many real situations both absorption and evolution of gas occur during the course of any given exposure. In such cases the volume changes which are recorded represent the net difference in volume change caused by the two reactions. Unless such reactions occur consecutively (as they sometimes do), the system does not evaluate their individual magnitudes as discrete processes.

Representative data is noted in Tables 1 through 4 using strip chart recorder 88. Tabulations of total volume change employ a negative sign (−) to indicate absorption of oxygen and a positive (+) sign to indicate gas evolution. When gas evolution or consumption in terms of moles/gram or rates in terms of moles/gram/min are calculated and the results graphically represented, the sign convention has been reversed. Thus, in the final compilation of the data, absorption is indicated by a positive sign and evolution by a negative one. All such calculations have been based upon an assumption that volume changes represent a net change in the oxygen content of the system. This assumption is reasonably valid for systems in which the chief reaction is one of absorption. However, when evolution of other gases occurs an error will be introduced by the assumption that observed changes represent solely variations in the oxygen content of the system. For uniformity, all data have been calculated as though oxygen were the only gas involved. Any conclusions drawn from the data should, however, include recognition of the fact that in some cases gases other than oxygen may be evolved. Note, however, that water and acid gases (carbon dioxide, formic acid, etc.) produced by oxygen absorption are not a problem since these are removed from the gas system by absorber 72 as they are formed.

TABLE 1

MLO-69-35
Oxygen Absorption Tests
at 400 deg. F., 215 ml/min. gas flow rate
Volume Changes, ml.

| TIME, MINUTES CUMULATIVE | RUN 1 (735.3 torr, 81 deg. F.) | RUN 2 (733.2 torr, 81 deg. F.) |
| --- | --- | --- |
| 0 | 0 | 0 |
| 15 | +17.2 | +12.0 |
| 30 | −57.0 | −61.6 |
| 45 | −63.0 | −63.7 |
| 60 | −57.8 | −61.9 |
| 75 | −59.5 | −58.6 |
| 90 | −47.7 | −67.4 |
| 105 | −44.6 | −61.4 |
| 120 | −52.0 | −71.4 |
| 135 | −38.2 | −55.3 |
| 150 | −34.1 | −49.8 |
| 165 | −37.4 | −44.0 |
| 180 | −34.8 | −52.4 |
| 195 | −34.2 | −47.4 |
| 210 | −33.3 | −55.9 |
| 225 | −33.6 | −32.9 |
| 240 | −31.8 | −39.8 |
| Net Change, ml. | −641.8 | −811.0 |

TABLE 2

MLO-69-35
Oxygen Absorption Tests
at 400 deg. F., 215 ml/min. gas flow rate
Oxygen Absorption, millimole/gram

| TIME, MINUTES CUMULATIVE | RUN 1 | RUN 2 |
| --- | --- | --- |
| 0 | — | — |
| 15 | −0.064 | −0.048 |
| 30 | +0.149 | +0.198 |
| 45 | +0.384 | +0.453 |
| 60 | +0.600 | +0.700 |
| 75 | +0.822 | +0.935 |
| 90 | +1.001 | +1.204 |
| 105 | +1.167 | +1.450 |
| 120 | +1.362 | +1.735 |
| 135 | +1.504 | +1.956 |
| 150 | +1.632 | +2.156 |
| 165 | +1.772 | +2.331 |
| 180 | +1.902 | +2.541 |
| 195 | +2.029 | +2.730 |
| 210 | +2.154 | +2.954 |
| 225 | +2.279 | +3.086 |
| 240 | +2.398 | +3.245 |

TABLE 3

MLO-69-35
Oxygen Absorption Tests
at 400 deg. F., 215 ml/min. gas flow rate
Oxygen Absorption Rate, micromoles/gram/min.

| TIME INTERVAL, MINUTES | RUN 1 | RUN 2 |
| --- | --- | --- |
| 0–15 | −4.28 | −3.20 |
| 15–30 | +14.20 | +16.42 |
| 30–45 | +15.69 | +16.98 |
| 45–60 | +14.40 | +16.50 |
| 60–75 | +14.82 | +15.62 |
| 75–90 | +11.88 | +17.97 |
| 90–105 | +11.11 | +16.37 |
| 105–120 | +12.95 | +19.03 |
| 120–135 | +9.52 | +14.74 |
| 135–150 | +8.49 | +13.27 |
| 150–165 | +9.32 | +11.73 |
| 165–180 | +8.67 | +13.97 |
| 180–195 | +8.52 | +12.63 |
| 195–210 | +8.30 | +14.90 |
| 210–225 | +8.37 | +8.77 |
| 225–240 | +7.92 | +10.61 |

TABLE 4

MLO-69-35
Oxygen Absorption Tests
at 400 deg. F., 215 ml/min. gas flow rate
Oil Properties after Oxygen Absorption Test

| | RUN 1 | RUN 2 |
| --- | --- | --- |
| Weight of Sample Used, grams | 10.530 | 9.812 |
| Weight of Condensate, grams | | |
| Ambient Trap | 0.4345 | 0.4166 |
| Cold Trap | 0.2673 | |

Initial studies with MLO-71-6, a fluorocarbon, indicated that little, if any, oxygen absorption occurred at 650° F. for the uncatalyzed sample. In the present case the reactions of that sample with oxygen in the presence of several metal catalysts have been evaluated by the oxygen absorption technique. Nine catalysts have been studied. Of these five were found to be essentially unreactive toward oxygen during the four-hour exposure period. The unreactive catalysts were: titanium, titanium SAL 4B, M-2 Steel, M-10 Steel and M-50 Steel. Evolution of gas was observed for all samples but particularly for the three steel samples. The gas evoluton especially manifested itself by a strong attack on glass components of the test system. It was apparent from the data that at least three and probably all of the unreactive sytems were beginning to absorb oxygen at the end of the test period. It was equally evident that absorption was in some cases at least probably concealed in its initial stages by the competing reaction which lead to the evolution of acid gas. Recovery of the acid gases so produced was not possible because of their reactivity towards the glass components.

Two of the catalysts—Titanium 4AL 4MN and 440C—were found to be moderately active with respect to the sample under the conditions of the test. Two other catalysts—410 and 52100 Steels—were quite active with respect to the inducing of absorption of oxygen by the sample.

The experimental data obtained with the manual system 10 for MLO-71-6 and the several catalysts which have been studied clearly indicate the need for longer term oxygen absorption studies. In several cases described above the induction period for oxygen absorption appeared to have just been completed at the end of the manual test.

Figure 4:
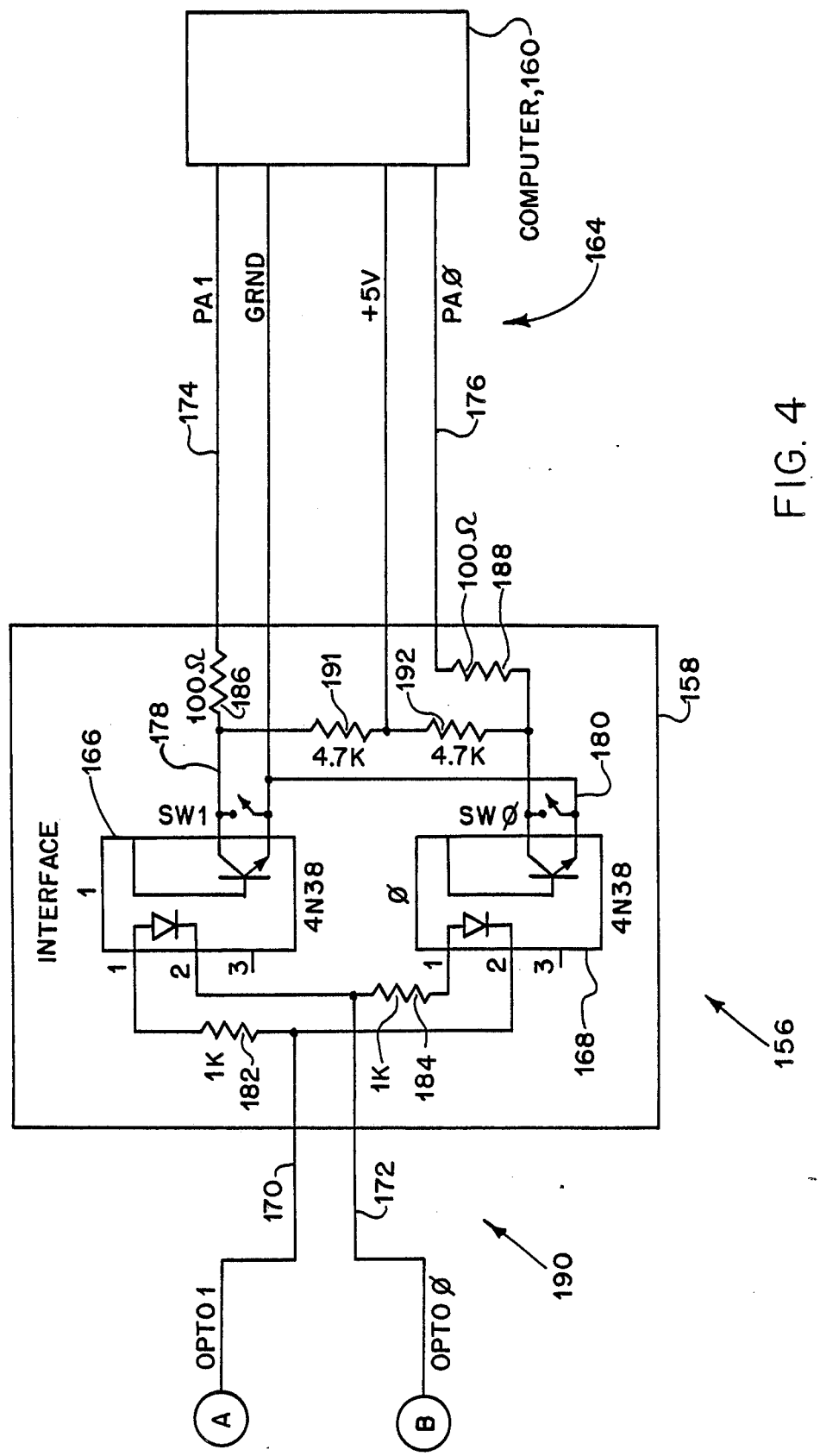
FIG. 4 is a schematic of the interface device connecting the computer to the electronics of FIG. 3.

To further improve the operability of automatic oxygen absorption measuring system 12, recorder 88 is replaced with an automatic data recording means 156 shown in FIG. 4 having an interface 158 and computer 160. Referring to FIG. 3, the ±3 millivolts applied to relays 74 and 76 is changed so that +0 volts is applied at the Y contacts 122 and 146, and +12 volts is applied at the X contacts 130 and 154. The voltage output on "A" movable arm 114 and "B" movable arm 138 depends upon whether relays 74 and 76, respectively, are activated.

Referring to FIG. 4 and to Table 5, interface 158 is provided to isolate the inputs 164 to computer 160 from potential voltage damage. Interface 158 has therein two opto-isolators 166 and 168 being Motorola 4N38 devices. Interface 158 receives input signals from OPTO 1 line 170 and OPTO Ø line 172 being a nominal 12 vdc. Depending on the differential voltage status on lines 170 and 172, refer to Table 5, opto-isolators 166 and 168 will invert the respective signal and convert it to a standard TTL logic level on output lines PA 1, 174, and PA Ø, 176, to computer 160. Test switches SW 1, 178, and SW Ø, 180, are provided to simulate relay 74 and relay 76 status.

Note that two 1 Kohm resistors 182 and 184 and two 100 ohm resistors 186 and 188 are provided in series with inputs 190 and outputs 164 of the opto-isolators respectively for current limiting. Two 4.7 Kohm resistors 191 and 192 are provided at the outputs 164 to "pull-up" the outputs to 5 v when not activated.

Computer 160 consists of an AIM-65 microcomputer with a custom interrupt-driven program located in PROM and interface 158 for connecting the AIM-65 to oxygen absorption measuring apparatus 12. A custom program in PROM includes a real-time calendar-clock routine and two elapsed seconds timers. The initialization of the calendar and/or clock is optional. The first elapsed seconds timer will track total seconds since the experiment began. The other timer will track total elapsed seconds since the last event occurred. The custom PROM is located at hexadecimal address D000 on the main board of the AIM-65. A complete assembly listing of the program PROM is listed in Table 6. It should be noted that the present invention may be used for the measurement of oxygen absorption from air as well as from a pure oxygen environment. If the initial purge steps are omitted and the system is flushed with air initially, the absorption medium will have the composition of air. Oxygen loss will be replaced by pure oxygen so that the net composition of the gaseous medium will remain unchanged—namely, if it was air to begin with, it will retain the composition of air; and if it was oxygen to begin with, it will remain as oxygen.

Data obtained with computer 160 is further illustrated in Tables 7 to 12 for two samples.

TABLE 5

SIGNAL SYSTEM KEY

| RELAY 1 | RELAY 2 | OPTO 1 | OPTO 0 | PA1 | PA0 | STATUS |
|---|---|---|---|---|---|---|
| Closed | Closed | 0 v | +12 v | +5 v | 0 v | Pressure High - Vent Cycle |
| Open | Closed | +12 v | +12 v | +5 v | +5 v | Normal |
| Open | Open | +12 v | 0 v | 0 v | +5 v | Pressure Low - Fill Cycle |

TABLE 6

```
D000:       1            ORG     *D000
E97A:       2  OUTPUT:   EQU     *E97A
F000:       3  OUTPRI:   EQU     *F000
EB9E:       4  PHXY:     EQU     *EB9E
EBAC:       5  PLXY:     EQU     *EBAC
A411:       6  PRIFLG:   EQU     *A411
E93C:       7  READ:     EQU     *E93C
FE96:       8  RED1:     EQU     *FE96
EB44:       9  CLR:      EQU     *EB44
EA13:      10  CRLOW:    EQU     *EA13
EF7B:      11  OUTDD1:   EQU     *EF7B
0F00:      12  YEAR:     EQU     *0F00
0F01:      13  MONTH:    EQU     *0F01
0F02:      14  DAY:      EQU     *0F02
0F03:      15  HOUR:     EQU     *0F03
0F04:      16  MIN:      EQU     *0F04
0F05:      17  SEC:      EQU     *0F05
0F06:      18  SEC1:     EQU     *0F06
0F07:      19  CNT0:     EQU     *0F07
0F08:      20  CNT1:     EQU     *0F08
0F09:      21  CNT2:     EQU     *0F09
0F0A:      22  CNT3:     EQU     *0F0A
0F0B:      23  CNT4:     EQU     *0F0B
0F0C:      24  XMONTH:   EQU     *0F0C
0F0D:      25  XDAY:     EQU     *0F0D
0F0E:      26  XHOUR:    EQU     *0F0E
```

```
OF0F:           27 XMIN:    EQU   $OF0F
OF10:           28 XSEC:    EQU   $OF10
OF11:           29 XSEC1:   EQU   $OF11
OF12:           30 XCNT0:   EQU   $OF12
OF13:           31 XCNT1:   EQU   $OF13
OF14:           32 XCNT2:   EQU   $OF14
OF15:           33 XCNT3:   EQU   $OF15
OF16:           34 XCNT4:   EQU   $OF16
OF17:           35 DATE:    EQU   $OF17
OF18:           36 TIME:    EQU   $OF18
OF19:           37 CHAR1:   EQU   $OF19
OF1A:           38 CHAR2:   EQU   $OF1A
OF1B:           39 CHAR3:   EQU   $OF1B
OF1C:           40 XYEAR:   EQU   $OF1C
OF1D:           41 GARB:    EQU   $OF1D
OF1E:           42 YCNT0:   EQU   $OF1E
OF1F:           43 YCNT1:   EQU   $OF1F
OF20:           44 YCNT2:   EQU   $OF20
OF21:           45 YCNT3:   EQU   $OF21
OF22:           46 YCNT4:   EQU   $OF22
OF23:           47 ZCNT0:   EQU   $OF23
OF24:           48 ZCNT1:   EQU   $OF24
OF25:           49 ZCNT2:   EQU   $OF25
OF26:           50 ZCNT3:   EQU   $OF26
OF27:           51 GARBX:   EQU   $OF27
OF28:           52 INTFLG:  EQU   $OF28
OF29:           53 DISBUF:  EQU   $OF29
A001:           54 PIA:     EQU   $A001
A004:           55 T1L:     EQU   $A004
A005:           56 T1H:     EQU   $A005
A00B:           57 ACR:     EQU   $A00B
A00D:           58 IFR:     EQU   $A00D
A00E:           59 IER:     EQU   $A00E
A480:           60 KBPIAA:  EQU   $A480
A482:           61 KBPIAB:  EQU   $A482
A400:           62 IRQV1:   EQU   $A400
A401:           63 IRQV2:   EQU   $A401
D000:           64          MSB   OFF
D000:A9 00      65          LDA   #0
D002:8D 11 A4   66          STA   PRIFLG
D005:78         67          SEI
D006:20 40 D6   68          JSR   ERASE
D009:A2 00      69 TIMST:   LDX   #0
D00B:A9 00      70 START:   LDA   #0
D00D:9D 00 OF   71          STA   YEAR,X
D010:E8         72          INX
D011:E0 2A      73          CPX   #42
D013:D0 F6      74          BNE   START
D015:A2 00      75          LDX   #0
D017:A9 01      76          LDA   #1
D019:8D 18 OF   77          STA   TIME
D01C:BD DD D6   78 TIMESG:  LDA   TIMSG,X
D01F:20 7A E9   79          JSR   OUTPUT
D022:E8         80          INX
D023:E0 0C      81          CPX   #12
D025:D0 F5      82          BNE   TIMSG
D027:20 96 FE   83 TIMIN:   JSR   RED1
D02A:C9 0D      84          CMP   #13
D02C:D0 20      85          BNE   TEST
D02E:A9 4E      86          LDA   #49998
```

```
D0030:8D 04 A0    87          STA    T1L
D0033:A9 C3       88          LDA    #49998/256
D0035:8D 05 A0    89          STA    T1H
D0038:A9 C0       90          LDA    #$C0
D003A:8D 0B A0    91          STA    ACR
D003D:8D 0E A0    92          STA    IER
D0040:A9 CD       93          LDA    #INT
D0042:8D 00 A4    94          STA    IRQV1
D0045:A9 D3       95          LDA    #<INT
D0047:8D 01 A4    96          STA    IRQV2
D004A:58          97          CLI
D004B:4C 52 D2    98          JMP    ALLOK
D004E:A0 00       99  TEST:   LDY    #0
D0050:8C 18 0F   100          STY    TIME
D0053:20 EF D4   101          JSR    NUMCHK
D0056:90 03      102          BCC    GOOD
D0058:4C C1 D6   103          JMP    ERROR
D005B:20 E8 D4   104  GOOD:   JSR    CNVT
D005E:8D 03 0F   105          STA    HOUR
D0061:20 96 FE   106          JSR    RED1
D0064:C9 3A      107          CMP    #':'
D0066:F0 31      108          BEQ    MININ
D0068:20 EF D4   109          JSR    NUMCHK
D006B:90 03      110          BCC    STORE
D006D:4C C1 D6   111          JMP    ERROR
D0070:20 E8 D4   112  STORE:  JSR    CNVT
D0073:48         113          PHA
D0074:AD 03 0F   114          LDA    HOUR
D0077:0A         115          ASL    A
D0078:0A         116          ASL    A
D0079:0A         117          ASL    A
D007A:0A         118          ASL    A
D007B:8D 03 0F   119          STA    HOUR
D007E:68         120          PLA
D007F:0D 03 0F   121          ORA    HOUR
D0082:8D 03 0F   122          STA    HOUR
D0085:C9 24      123          CMP    #$24
D0087:10 03      124          BPL    NOTGOOD
D0089:4C 8F D0   125          JMP    COLON
D008C:4C C1 D6   126  NOTGOOD: JMP   ERROR
D008F:20 96 FE   127  COLON:  JSR    RED1
D0092:C9 3A      128          CMP    #':'
D0094:F0 03      129          BEQ    MININ
D0096:4C C1 D6   130          JMP    ERROR
D0099:20 96 FE   131  MININ:  JSR    RED1
D009C:20 EF D4   132          JSR    NUMCHK
D009F:90 03      133          BCC    GOOD1
D00A1:4C C1 D6   134          JMP    ERROR
D00A4:20 E8 D4   135  GOOD1:  JSR    CNVT
D00A7:8D 04 0F   136          STA    MIN
D00AA:20 96 FE   137          JSR    RED1
D00AD:C9 3A      138          CMP    #':'
D00AF:F0 2B      139          BEQ    SECIN
D00B1:20 EF D4   140          JSR    NUMCHK
D00B4:90 03      141          BCC    STORMIN
D00B6:4C C1 D6   142          JMP    ERROR
D00B9:20 E8 D4   143  STORMIN: JSR   CNVT
D00BC:48         144          PHA
D00BD:AD 04 0F   145          LDA    MIN
D00C0:0A         146          ASL    A
```

D089: 4C  8F  D0
D08C: 4C  C1  D6
D08F: 20  96  FE
D092: C9  3A

```
D0C1:0A            147         ASL   A
D0C2:0A            148         ASL   A
D0C3:0A            149         ASL   A
D0C4:8D 04 0F      150         STA   MIN
D0C7:68            151         PLA
D0C8:0D 04 0F      152         ORA   MIN
D0CB:8D 04 0F      153         STA   MIN
D0CE:C9 60         154         CMP   #$60
D0D0:10 BA         155         BPL   NOTGOOD
D0D2:20 96 FE      156 COLON1: JSR   RED1
D0D5:C9 3A         157         CMP   #':'
D0D7:F0 03         158         BEQ   SECIN
D0D9:4C C1 D6      159         JMP   ERROR
D0DC:20 96 FE      160 SECIN:  JSR   RED1
D0DF:20 EF D4      161         JSR   NUMCHK
D0E2:90 03         162         BCC   GOOD2
D0E4:4C C1 D6      163         JMP   ERROR
D0E7:20 E8 D4      164 GOOD2:  JSR   CNVT
D0EA:8D 05 0F      165         STA   SEC
D0ED:20 96 FE      166         JSR   RED1
D0F0:20 EF D4      167         JSR   NUMCHK
D0F3:90 03         168         BCC   STORSEC
D0F5:4C C1 D6      169 ER:     JMP   ERROR
D0F8:20 E8 D4      170 STORSEC: JSR  CNVT
D0FB:48            171         PHA
D0FC:AD 05 0F      172         LDA   SEC
D0FF:0A            173         ASL   A
D100:0A            174         ASL   A
D101:0A            175         ASL   A
D102:0A            176         ASL   A
D103:8D 05 0F      177         STA   SEC
D106:68            178         PLA
D107:0D 05 0F      179         ORA   SEC
D10A:8D 05 0F      180         STA   SEC
D10D:C9 60         181         CMP   #$60
D10F:10 E4         182         BPL   ER
D111:A9 4E         183         LDA   #49998
D113:8D 04 A0      184         STA   T1L
D116:A9 C3         185         LDA   #49998/256
D118:8D 05 A0      186         STA   T1H
D11B:A9 C0         187         LDA   #$C0
D11D:8D 0B A0      188         STA   ACR
D120:8D 0E A0      189         STA   IER
D123:A9 CD         190         LDA   #INT
D125:8D 00 A4      191         STA   IRQV1
D128:A9 D3         192         LDA   #<INT
D12A:8D 01 A4      193         STA   IRQV2
D12D:58            194         CLI
D12E:A9 01         195 DATST:  LDA   #1
D130:8D 17 0F      196         STA   DATE
D133:20 40 D6      197         JSR   ERASE
D136:A2 00         198         LDX   #0
D138:BD 6C D6      199 DSTR:   LDA   DATEST,X
D13B:C9 2A         200         CMP   #'*'
D13D:F0 07         201         BEQ   DSTR1
D13F:20 7A E9      202         JSR   OUTPUT
D142:E8            203         INX
D143:4C 38 D1      204         JMP   DSTR
D146:20 96 FE      205 DSTR1:  JSR   RED1
D149:C9 0D         206         CMP   #13
```

D125: 8D 00 A4
D128: A9 D3
D12A: 8D 01 A4
D12D: 58

```
D14B:D0 03        207            BNE    NOTFIN
D14D:4C 52 D2     208            JMP    ALLOK
D150:A0 00        209  NOTFIN:   LDY    #0
D152:8C 17 0F     210            STY    DATE
D155:20 EF D4     211            JSR    NUMCHK
D158:90 03        212            BCC    OK1
D15A:4C 8D D6     213            JMP    ERR
D15D:20 E8 D4     214  OK1:      JSR    CNVT
D160:8D 02 0F     215            STA    DAY
D163:20 96 FE     216            JSR    RED1
D166:C9 2D        217            CMP    #'-'
D168:F0 2E        218            BEQ    MOIN
D16A:20 EF D4     219            JSR    NUMCHK
D16D:90 03        220            BCC    OK2
D16F:4C 8D D6     221            JMP    ERR
D172:20 E8 D4     222  OK2:      JSR    CNVT
D175:48           223            PHA
D176:AD 02 0F     224            LDA    DAY
D179:0A           225            ASL    A
D17A:0A           226            ASL    A
D17B:0A           227            ASL    A
D17C:0A           228            ASL    A
D17D:8D 02 0F     229            STA    DAY
D180:68           230            PLA
D181:0D 02 0F     231            ORA    DAY
D184:8D 02 0F     232            STA    DAY
D187:C9 32        233            CMP    #$32
D189:30 03        234            BMI    OK3
D18B:4C 8D D6     235            JMP    ERR
D18E:20 96 FE     236  OK3:      JSR    RED1
D191:C9 2D        237            CMP    #'-'
D193:F0 03        238            BEQ    MOIN
D195:4C 8D D6     239            JMP    ERR
D198:20 96 FE     240  MOIN:     JSR    RED1
D19B:20 DC D4     241            JSR    LETCHK
D19E:90 03        242            BCC    OK4
D1A0:4C 8D D6     243            JMP    ERR
D1A3:8D 19 0F     244  OK4:      STA    CHAR1
D1A6:20 96 FE     245            JSR    RED1
D1A9:20 DC D4     246            JSR    LETCHK
D1AC:90 03        247            BCC    OK5
D1AE:4C 8D D6     248            JMP    ERR
D1B1:8D 1A 0F     249  OK5:      STA    CHAR2
D1B4:20 96 FE     250            JSR    RED1
D1B7:20 DC D4     251            JSR    LETCHK
D1BA:90 03        252            BCC    OK6
D1BC:4C 8D D6     253            JMP    ERR
D1BF:8D 1B 0F     254  OK6:      STA    CHAR3
D1C2:A2 00        255            LDX    #0
D1C4:A9 01        256            LDA    #1
D1C6:8D 01 0F     257            STA    MONTH
D1C9:AD 19 0F     258  MOCHK:    LDA    CHAR1
D1CC:DD FB D4     259            CMP    MONTAB,X
D1CF:D0 10        260            BNE    NOTR
D1D1:AD 1A 0F     261            LDA    CHAR2
D1D4:DD FC D4     262            CMP    MONTAB+1,X
D1D7:D0 08        263            BNE    NOTR
D1D9:AD 1B 0F     264            LDA    CHAR3
D1DC:DD FD D4     265            CMP    MONTAB+2,X
D1DF:F0 18        266            BEQ    OKAY
```

```
 D1E1:E8              267 NOTR:   INX
 D1E2:E8              268         INX
 D1E3:E8              269         INX
 D1E4:AD 01 OF        270         LDA    MONTH
 D1E7:18              271         CLC
 D1E8:F8              272         SED
 D1E9:69 01           273         ADC    #1
 D1EB:8D 01 OF        274         STA    MONTH
 D1EE:D8              275         CLD
 D1EF:E0 24           276         CPX    #36
 D1F1:D0 03           277         BNE    OK7
 D1F3:4C 8D D6        278         JMP    ERR
 D1F6:4C C9 D1        279 OK7:    JMP    MOCHK
 D1F9:20 96 FE        280 OKAY:   JSR    RED1
 D1FC:C9 2D           281         CMP    #'-'
 D1FE:F0 03           282         BEQ    OK8
 D200:4C 8D D6        283         JMP    ERR
 D203:20 96 FE        284 OK8:    JSR    RED1
 D206:20 EF D4        285         JSR    NUMCHK
 D209:90 03           286         BCC    OK9
 D20B:4C 8D D6        287         JMP    ERR
 D20E:20 E8 D4        288 OK9:    JSR    CNVT
 D211:0A              289         ASL    A
 D212:0A              290         ASL    A
 D213:0A              291         ASL    A
 D214:0A              292         ASL    A
 D215:8D 00 OF        293         STA    YEAR
 D218:20 96 FE        294         JSR    RED1
 D21B:20 EF D4        295         JSR    NUMCHK
 D21E:90 03           296         BCC    OK10
 D220:4C 8D D6        297         JMP    ERR
 D223:20 E8 D4        298 OK10:   JSR    CNVT
 D226:0D 00 OF        299         ORA    YEAR
 D229:8D 00 OF        300         STA    YEAR
 D22C:AD 01 OF        301         LDA    MONTH
 D22F:20 12 D6        302         JSR    DECONV
 D232:AA              303         TAX
 D233:CA              304         DEX
 D234:BD D0 D4        305         LDA    DAYTAB,X
 D237:CD 02 OF        306         CMP    DAY
 D23A:10 03           307         BPL    OK11
 D23C:4C 8D D6        308         JMP    ERR
 D23F:C9 29           309 OK11:   CMP    #$29
 D241:D0 0F           310         BNE    ALLOK
 D243:AD 02 OF        311         LDA    DAY
 D246:C9 29           312         CMP    #$29
 D248:D0 08           313         BNE    ALLOK
 D24A:20 2D D6        314         JSR    LEAP
 D24D:90 03           315         BCC    ALLOK
 D24F:4C 8D D6        316         JMP    ERR
 D252:EA              317 ALLOK:  NOP
 D253:20 40 D6        318 CLOCK:  JSR    ERASE
 D256:A2 00           319         LDX    #0
 D258:BD 4C D7        320 PROMPT: LDA    MESS,X
 D25B:C9 2A           321         CMP    #'*'
 D25D:F0 07           322         BEQ    EXIT
 D25F:E8              323         INX
 D260:20 7A E9        324         JSR    OUTPUT
 D263:4C 58 D2        325         JMP    PROMPT
 D266:20 96 FE        326 EXIT:   JSR    RED1
```

```
D269:C9 0D       327         CMP   #13
D26B:D0 E6       328         BNE   CLOCK
D26D:20 40 D6    329         JSR   ERASE
D270:78          330         SEI
D271:A9 00       331         LDA   #0
D273:8D 07 0F    332         STA   CNT0
D276:8D 08 0F    333         STA   CNT1
D279:8D 09 0F    334         STA   CNT2
D27C:8D 0A 0F    335         STA   CNT3
D27F:8D 0B 0F    336         STA   CNT4
D282:8D 23 0F    337         STA   ZCNT0
D285:8D 24 0F    338         STA   ZCNT1
D288:8D 25 0F    339         STA   ZCNT2
D28B:8D 26 0F    340         STA   ZCNT3
D28E:58          341         CLI
D28F:20 36 D5    342 MAIN:   JSR   DISPLAY
D292:A9 DF       343         LDA   #$DF
D294:8D 80 A4    344         STA   KBPIAA
D297:AD 82 A4    345         LDA   KBPIAB
D29A:29 80       346         AND   #$80
D29C:D0 03       347         BNE   NOBRK
D29E:4C 53 D2    348         JMP   CLOCK
D2A1:A9 03       349 NOBRK:  LDA   #3
D2A3:2D 01 A0    350         AND   PIA
D2A6:49 03       351         EOR   #3
D2A8:EA          352         NOP
D2A9:EA          353         NOP
D2AA:F0 E3       354         BEQ   MAIN
D2AC:A9 01       355         LDA   #1
D2AE:2D 01 A0    356         AND   PIA
D2B1:49 01       357         EOR   #1
D2B3:EA          358         NOP
D2B4:EA          359         NOP
D2B5:D0 06       360         BNE   MINUS
D2B7:20 DF D2    361 PLUS:   JSR   LOGP
D2BA:4C C0 D2    362         JMP   QUIET
D2BD:20 E4 D2    363 MINUS:  JSR   LOGN
D2C0:20 36 D5    364 QUIET:  JSR   DISPLAY
D2C3:A9 03       365         LDA   #3
D2C5:2D 01 A0    366         AND   PIA
D2C8:49 03       367         EOR   #3
D2CA:EA          368         NOP
D2CB:EA          369         NOP
D2CC:D0 F2       370         BNE   QUIET
D2CE:20 36 D5    371         JSR   DISPLAY
D2D1:A9 03       372         LDA   #3
D2D3:2D 01 A0    373         AND   PIA
D2D6:49 03       374         EOR   #3
D2D8:EA          375         NOP
D2D9:EA          376         NOP
D2DA:D0 E4       377         BNE   QUIET
D2DC:4C 8F D2    378         JMP   MAIN
D2DF:A9 2B       379 LOGP:   LDA   #'+'
D2E1:4C E6 D2    380         JMP   LOG
D2E4:A9 2D       381 LOGN:   LDA   #'-'
D2E6:48          382 LOG:    PHA
D2E7:20 E9 D6    383         JSR   COPY
D2EA:78          384         SEI
D2EB:A9 00       385         LDA   #0
D2ED:8D 23 0F    386         STA   ZCNT0
```

```
D2F0:8D 24 OF   387         STA     ZCNT1
D2F3:8D 25 OF   388         STA     ZCNT2
D2F6:8D 26 OF   389         STA     ZCNT3
D2F9:A9 80      390         LDA     #$80
D2FB:8D 11 A4   391         STA     PRIFLG
D2FE:68         392         PLA
D2FF:20 00 F0   393         JSR     OUTPRI
D302:A9 0D      394         LDA     #13
D304:20 00 F0   395         JSR     OUTPRI
D307:A0 00      396         LDY     #0
D309:AD 16 OF   397         LDA     XCNT4
D30C:20 61 D7   398         JSR     POUT
D30F:AD 15 OF   399         LDA     XCNT3
D312:20 61 D7   400         JSR     POUT
D315:AD 14 OF   401         LDA     XCNT2
D318:20 61 D7   402         JSR     POUT
D31B:AD 13 OF   403         LDA     XCNT1
D31E:20 61 D7   404         JSR     POUT
D321:A9 2E      405         LDA     #'.'
D323:20 00 F0   406         JSR     OUTPRI
D326:AD 12 OF   407         LDA     XCNT0
D329:20 61 D7   408         JSR     POUT
D32C:A9 20      409         LDA     #' '
D32E:20 00 F0   410         JSR     OUTPRI
D331:AD 21 OF   411         LDA     YCNT3
D334:20 61 D7   412         JSR     POUT
D337:AD 20 OF   413         LDA     YCNT2
D33A:20 61 D7   414         JSR     POUT
D33D:AD 1F OF   415         LDA     YCNT1
D340:20 61 D7   416         JSR     POUT
D343:A9 2E      417         LDA     #'.'
D345:20 00 F0   418         JSR     OUTPRI
D348:A0 06      419         LDY     #6
D34A:AD 1E OF   420         LDA     YCNT0
D34D:20 61 D7   421         JSR     POUT
D350:20 7D D7   422         JSR     ADD1
D353:AC 18 OF   423         LDY     TIME
D356:C0 01      424         CPY     #1
D358:D0 0F      425         BNE     PRINT
D35A:A9 0D      426 LF:     LDA     #13
D35C:20 00 F0   427         JSR     OUTPRI
D35F:20 00 F0   428         JSR     OUTPRI
D362:58         429         CLI
D363:A9 00      430         LDA     #0
D365:8D 11 A4   431         STA     PRIFLG
D368:60         432         RTS
D369:AD 0E OF   433 PRINT:  LDA     XHOUR
D36C:20 61 D7   434         JSR     POUT
D36F:A9 3A      435         LDA     #':'
D371:20 00 F0   436         JSR     OUTPRI
D374:AD 0F OF   437         LDA     XMIN
D377:20 61 D7   438         JSR     POUT
D37A:A9 3A      439         LDA     #':'
D37C:20 00 F0   440         JSR     OUTPRI
D37F:AD 10 OF   441         LDA     XSEC
D382:20 61 D7   442         JSR     POUT
D385:20 7D D7   443         JSR     ADD1
D388:AC 17 OF   444         LDY     DATE
D38B:C0 01      445         CPY     #1
D38D:D0 03      446         BNE     PRDAT
```

D2F6: 8D 26 OF
D2F9: A9 80
D2FB: 8D 11 A4
D2FE: 68

```
D38F:4C 5A D3   447            JMP   LF
D392:A9 20      448    PRDAT:  LDA   #' '
D394:20 00 F0   449            JSR   OUTPRI
D397:AD 0D 0F   450            LDA   XDAY
D39A:20 61 D7   451            JSR   POUT
D39D:A9 2D      452            LDA   #'-'
D39F:20 00 F0   453            JSR   OUTPRI
D3A2:20 88 D7   454            JSR   CHRMON
D3A5:B9 FB D4   455            LDA   MONTAB,Y
D3A8:20 00 F0   456            JSR   OUTPRI
D3AB:B9 FC D4   457            LDA   MONTAB+1,Y
D3AE:20 00 F0   458            JSR   OUTPRI
D3B1:B9 FD D4   459            LDA   MONTAB+2,Y
D3B4:20 00 F0   460            JSR   OUTPRI
D3B7:A9 2D      461            LDA   #'-'
D3B9:20 00 F0   462            JSR   OUTPRI
D3BC:A0 00      463            LDY   #0
D3BE:AD 1C 0F   464            LDA   XYEAR
D3C1:20 61 D7   465            JSR   POUT
D3C4:4C 5A D3   466            JMP   LF
D3C7:A9 01      467    INTX:   LDA   #1
D3C9:8D 28 0F   468            STA   INTFLG
D3CC:08         469            PHP
D3CD:F8         470    INT:    SED
D3CE:48         471            PHA
D3CF:20 9E EB   472            JSR   PHXY
D3D2:AD 07 0F   473            LDA   CNT0
D3D5:18         474            CLC
D3D6:69 05      475            ADC   #5
D3D8:8D 07 0F   476            STA   CNT0
D3DB:90 26      477            BCC   SKIP1
D3DD:AD 08 0F   478            LDA   CNT1
D3E0:69 00      479            ADC   #0
D3E2:8D 08 0F   480            STA   CNT1
D3E5:90 1C      481            BCC   SKIP1
D3E7:AD 09 0F   482            LDA   CNT2
D3EA:69 00      483            ADC   #0
D3EC:8D 09 0F   484            STA   CNT2
D3EF:90 12      485            BCC   SKIP1
D3F1:AD 0A 0F   486            LDA   CNT3
D3F4:69 00      487            ADC   #0
D3F6:8D 0A 0F   488            STA   CNT3
D3F9:90 08      489            BCC   SKIP1
D3FB:AD 0B 0F   490            LDA   CNT4
D3FE:69 00      491            ADC   #0
D400:8D 0B 0F   492            STA   CNT4
D403:AD 23 0F   493    SKIP1:  LDA   ZCNT0
D406:18         494            CLC
D407:69 05      495            ADC   #5
D409:8D 23 0F   496            STA   ZCNT0
D40C:90 1C      497            BCC   SKIP5
D40E:AD 24 0F   498            LDA   ZCNT1
D411:69 00      499            ADC   #0
D413:8D 24 0F   500            STA   ZCNT1
D416:90 12      501            BCC   SKIP5
D418:AD 25 0F   502            LDA   ZCNT2
D41B:69 00      503            ADC   #0
D41D:8D 25 0F   504            STA   ZCNT2
D420:90 08      505            BCC   SKIP5
```

D3A5: B9 FB D4
D3A8: 20 00 F0
D3AB: B9 FC D4
D3AE: 20 00 F0
D3B1: B9 FD D4

```
D422:AD 26 OF   506            LDA   ZCNT3
D425:69 00      507            ADC   #0
D427:8D 26 OF   508            STA   ZCNT3
D42A:AD 06 OF   509 SKIP5:     LDA   SEC1
D42D:18         510            CLC
D42E:69 05      511            ADC   #5
D430:8D 06 OF   512            STA   SEC1
D433:B0 03      513            BCS   SKIP3
D435:4C BA D4   514 SKIP4:     JMP   SKIP2
D438:AD 05 OF   515 SKIP3:     LDA   SEC
D43B:69 00      516            ADC   #0
D43D:8D 05 OF   517            STA   SEC
D440:C9 60      518            CMP   #$60
D442:D0 F1      519            BNE   SKIP4
D444:A9 00      520            LDA   #0
D446:8D 05 OF   521            STA   SEC
D449:AD 04 OF   522            LDA   MIN
D44C:18         523            CLC
D44D:69 01      524            ADC   #1
D44F:8D 04 OF   525            STA   MIN
D452:C9 60      526            CMP   #$60
D454:D0 64      527            BNE   SKIP2
D456:A9 00      528            LDA   #0
D458:8D 04 OF   529            STA   MIN
D45B:AD 03 OF   530            LDA   HOUR
D45E:18         531            CLC
D45F:69 01      532            ADC   #1
D461:8D 03 OF   533            STA   HOUR
D464:C9 24      534            CMP   #$24
D466:D0 52      535            BNE   SKIP2
D468:A9 00      536            LDA   #0
D46A:8D 03 OF   537            STA   HOUR
D46D:AD 02 OF   538            LDA   DAY
D470:18         539            CLC
D471:69 01      540            ADC   #1
D473:8D 02 OF   541            STA   DAY
D476:AD 01 OF   542            LDA   MONTH
D479:20 12 D6   543            JSR   DECONV
D47C:AA         544            TAX
D47D:CA         545            DEX
D47E:BD D0 D4   546            LDA   DAYTAB,X
D481:CD 02 OF   547            CMP   DAY
D484:30 14      548            BMI   NEWMON
D486:C9 29      549            CMP   #$29
D488:D0 30      550            BNE   SKIP2
D48A:AD 02 OF   551            LDA   DAY
D48D:C9 29      552            CMP   #$29
D48F:D0 29      553            BNE   SKIP2
D491:20 2D D6   554            JSR   LEAP
D494:F8         555            SED
D495:B0 03      556            BCS   NEWMON
D497:4C BA D4   557            JMP   SKIP2
D49A:A9 01      558 NEWMON:    LDA   #1
D49C:8D 02 OF   559            STA   DAY
D49F:18         560            CLC
D4A0:AD 01 OF   561            LDA   MONTH
D4A3:69 01      562            ADC   #1
D4A5:8D 01 OF   563            STA   MONTH
D4A8:C9 13      564            CMP   #$13
D4AA:D0 0E      565            BNE   SKIP2
```

```
D4AC:A9 01        566         LDA    #1
D4AE:8D 01 OF     567         STA    MONTH
D4B1:AD 00 OF     568         LDA    YEAR
D4B4:18           569         CLC
D4B5:69 01        570         ADC    #1
D4B7:8D 00 OF     571         STA    YEAR
D4BA:AD 04 A0     572 SKIP2:  LDA    T1L
D4BD:20 AC EB     573         JSR    PLXY
D4C0:AD 28 OF     574         LDA    INTFLG
D4C3:F0 08        575         BEQ    INTRET
D4C5:A9 00        576         LDA    #0
D4C7:8D 28 OF     577         STA    INTFLG
D4CA:68           578         PLA
D4CB:28           579         PLP
D4CC:60           580         RTS
D4CD:68           581 INTRET: PLA
D4CE:D8           582         CLD
D4CF:40           583         RTI
D4D0:31 29 31     584 DAYTAB: DFB    $31,$29,$31,$30
D4D3:30
D4D4:31 30 31     585         DFB    $31,$30,$31,$31
D4D7:31
D4D8:30 31 30     586         DFB    $30,$31,$30,$31
D4DB:31
D4DC:C9 40        587 LETCHK: CMP    #'A'-1
D4DE:30 06        588         BMI    NOTLET
D4E0:C9 5B        589         CMP    #'Z'+1
D4E2:10 02        590         BPL    NOTLET
D4E4:18           591         CLC
D4E5:60           592         RTS
D4E6:38           593 NOTLET: SEC
D4E7:60           594         RTS
D4E8:08           595 CNVT:   PHP
D4E9:D8           596         CLD
D4EA:38           597         SEC
D4EB:E9 30        598         SBC    #48
D4ED:28           599         PLP
D4EE:60           600         RTS
D4EF:C9 3A        601 NUMCHK: CMP    #'9'+1
D4F1:10 06        602         BPL    NOTNUM
D4F3:C9 2F        603         CMP    #'0'-1
D4F5:30 02        604         BMI    NOTNUM
D4F7:18           605         CLC
D4F8:60           606         RTS
D4F9:38           607 NOTNUM: SEC
D4FA:60           608         RTS
D4FB:4A 41 4E     609 MONTAB: ASC    'JANFEBMARAPRMAYJUN'
D4FE:46 45 42
D501:4D 41 52
D504:41 50 52
D507:4D 41 59
D50A:4A 55 4E
D50D:4A 55 4C     610         ASC    'JULAUGSEPOCTNOVDEC'
D510:41 55 47
D513:53 45 50
D516:4F 43 54
D519:4E 4F 56
D51C:44 45 43
D51F:48           611 NUMOUT: PHA
D520:4A           612         LSR    A
```

```
D521:4A              613           LSR    A
D522:4A              614           LSR    A
D523:4A              615           LSR    A
D524:18              616           CLC
D525:69 30           617           ADC    #48
D527:9D 29 OF        618           STA    DISBUF,X
D52A:E8              619           INX
D52B:68              620           PLA
D52C:29 OF           621           AND    #$0F
D52E:18              622           CLC
D52F:69 30           623           ADC    #48
D531:9D 29 OF        624  LETOUT:  STA    DISBUF,X
D534:E8              625           INX
D535:60              626           RTS
D536:20 E9 D6        627  DISPLAY: JSR    COPY
D539:AD 18 OF        628           LDA    TIME
D53C:F0 03           629           BEQ    OKTIME
D53E:4C C8 D5        630           JMP    NOTIME
D541:A2 00           631  OKTIME:  LDX    #0
D543:AD 0E OF        632           LDA    XHOUR
D546:20 1F D5        633           JSR    NUMOUT
D549:A9 3A           634           LDA    #':'
D54B:20 31 D5        635           JSR    LETOUT
D54E:AD 0F OF        636           LDA    XMIN
D551:20 1F D5        637           JSR    NUMOUT
D554:A9 3A           638           LDA    #':'
D556:20 31 D5        639           JSR    LETOUT
D559:AD 10 OF        640           LDA    XSEC         D559: AD  10  OF
D55C:20 1F D5        641           JSR    NUMOUT       D55C: 20  1F  D5
D55F:A9 2E           642           LDA    #'.'         D55F: A9  2E
D561:20 31 D5        643           JSR    LETOUT       D561: 20  31  D5
D564:AD 11 OF        644           LDA    XSEC1
D567:20 1F D5        645           JSR    NUMOUT
D56A:CA              646           DEX
D56B:A9 20           647           LDA    #' '
D56D:20 31 D5        648           JSR    LETOUT
D570:AD 17 OF        649           LDA    DATE
D573:F0 0C           650           BEQ    DODATE
D575:A9 20           651  MOSP:    LDA    #' '
D577:20 31 D5        652           JSR    LETOUT
D57A:E0 14           653           CPX    #20
D57C:D0 F7           654           BNE    MOSP
D57E:4C B2 D5        655           JMP    DISOUT
D581:AD 0D OF        656  DODATE:  LDA    XDAY
D584:20 1F D5        657           JSR    NUMOUT
D587:A9 2D           658           LDA    #'-'
D589:20 31 D5        659           JSR    LETOUT
D58C:8E 27 OF        660           STX    GARBX
D58F:20 88 D7        661           JSR    CHRMON
D592:AE 27 OF        662           LDX    GARBX
D595:B9 FB D4        663           LDA    MONTAB,Y
D598:20 31 D5        664           JSR    LETOUT
D59B:B9 FC D4        665           LDA    MONTAB+1,Y
D59E:20 31 D5        666           JSR    LETOUT
D5A1:B9 FD D4        667           LDA    MONTAB+2,Y
D5A4:20 31 D5        668           JSR    LETOUT
D5A7:A9 2D           669           LDA    #'-'
D5A9:20 31 D5        670           JSR    LETOUT
D5AC:AD 1C OF        671           LDA    XYEAR
D5AF:20 1F D5        672           JSR    NUMOUT
```

```
D5B2:A2 00            673 DISOUT:  LDX    #0
D5B4:BD 29 OF         674 DISLOP:  LDA    DISBUF,X
D5B7:20 9E EB         675          JSR    PHXY
D5BA:09 80            676          ORA    #$80
D5BC:20 7B EF         677          JSR    OUTDD1
D5BF:20 AC EB         678          JSR    PLXY
D5C2:E8               679          INX
D5C3:E0 14            680          CPX    #20
D5C5:D0 ED            681          BNE    DISLOP
D5C7:60               682          RTS
D5C8:A2 00            683 NOTIME:  LDX    #0
D5CA:AD 16 OF         684          LDA    XCNT4
D5CD:20 1F D5         685          JSR    NUMOUT
D5D0:AD 15 OF         686          LDA    XCNT3
D5D3:20 1F D5         687          JSR    NUMOUT
D5D6:AD 14 OF         688          LDA    XCNT2
D5D9:20 1F D5         689          JSR    NUMOUT
D5DC:AD 13 OF         690          LDA    XCNT1
D5DF:20 1F D5         691          JSR    NUMOUT
D5E2:A9 2E            692          LDA    #'.'
D5E4:20 31 D5         693          JSR    LETOUT
D5E7:AD 12 OF         694          LDA    XCNT0
D5EA:20 1F D5         695          JSR    NUMOUT
D5ED:A9 20            696          LDA    #' '
D5EF:20 31 D5         697          JSR    LETOUT
D5F2:AD 21 OF         698          LDA    YCNT3
D5F5:20 1F D5         699          JSR    NUMOUT
D5F8:AD 20 OF         700          LDA    YCNT2
D5FB:20 1F D5         701          JSR    NUMOUT
D5FE:AD 1F OF         702          LDA    YCNT1
D601:20 1F D5         703          JSR    NUMOUT
D604:A9 2E            704          LDA    #'.'
D606:20 31 D5         705          JSR    LETOUT
D609:AD 1E OF         706          LDA    YCNT0
D60C:20 1F D5         707          JSR    NUMOUT
D60F:4C B2 D5         708          JMP    DISOUT
D612:08               709 DECONV:  PHP
D613:8D 1D OF         710          STA    GARB
D616:A9 10            711          LDA    #$10
D618:2C 1D OF         712          BIT    GARB
D61B:F0 0B            713          BEQ    LEAVE
D61D:D8               714          CLD
D61E:AD 1D OF         715          LDA    GARB
D621:29 EF            716          AND    #$EF
D623:18               717          CLC
D624:69 0A            718          ADC    #10
D626:28               719          PLP
D627:60               720          RTS
D628:AD 1D OF         721 LEAVE:   LDA    GARB
D62B:28               722          PLP
D62C:60               723          RTS
D62D:AD 00 OF         724 LEAP:    LDA    YEAR
D630:F8               725          SED
D631:38               726 LEAPL:   SEC
D632:F0 06            727          BEQ    YES
D634:E9 04            728          SBC    #4
D636:90 05            729          BCC    NO
D638:B0 F7            730          BCS    LEAPL
D63A:18               731 YES:     CLC
```

```
D63B:90 01      732           BCC    RET
D63D:38         733 NO:       SEC
D63E:D8         734 RET:      CLD
D63F:60         735           RTS
D640:20 44 EB   736 ERASE:    JSR    CLR
D643:A2 00      737           LDX    #0
D645:BD 57 D6   738 REP:      LDA    BLANK,X
D648:C9 2A      739           CMP    #'*'
D64A:F0 07      740           BEQ    DONE
D64C:20 7A E9   741           JSR    OUTPUT
D64F:E8         742           INX
D650:4C 45 D6   743           JMP    REP
D653:20 44 EB   744 DONE:     JSR    CLR
D656:60         745           RTS
D657:20 20 20   746 BLANK:    ASC    '
D65A:20 20 20
D65D:20 20 20
D660:20 20 20
D663:20 20 20
D666:20 20 20
D669:20 20 2A
D66C:45 4E 54   747 DATEST:   ASC    'ENTER    DATE:*'
D66F:45 52 20
D672:44 41 54
D675:45 3A 2A
D678:49 4E 50   748 ERMES:    ASC    'INPUT    ERROR,RE-ENTER*'
D67B:55 54 20
D67E:45 52 52
D681:4F 52 2C
D684:52 45 2D
D687:45 4E 54
D68A:45 52 2A
D68D:20 40 D6   749 ERR:      JSR    ERASE
D690:A2 00      750           LDX    #0
D692:BD 78 D6   751 ERRST:    LDA    ERMES,X
D695:C9 2A      752           CMP    #'*'
D697:F0 07      753           BEQ    FIN
D699:E8         754           INX
D69A:20 7A E9   755           JSR    OUTPUT
D69D:4C 92 D6   756           JMP    ERRST      D69D: 4C  92  D6
D6A0:20 A9 D6   757 FIN:      JSR    WAIT1      D6A0: 20  A9  D6
D6A3:20 40 D6   758           JSR    ERASE      D6A3: 20  40  D6
D6A6:4C 2E D1   759           JMP    DATST      D6A6: 4C  2E  D1
D6A9:A9 00      760 WAIT1:    LDA    #0         D6A9: A9  00
D6AB:A2 00      761           LDX    #0
D6AD:A0 04      762           LDY    #4
D6AF:38         763 W1:       SEC
D6B0:E9 01      764           SBC    #1
D6B2:F0 02      765           BEQ    W2
D6B4:D0 F9      766           BNE    W1
D6B6:CA         767 W2:       DEX
D6B7:F0 02      768           BEQ    W3
D6B9:D0 F4      769           BNE    W1
D6BB:88         770 W3:       DEY
D6BC:F0 02      771           BEQ    W4
D6BE:D0 EF      772           BNE    W1
D6C0:60         773 W4:       RTS
D6C1:20 40 D6   774 ERROR:    JSR    ERASE
D6C4:A2 00      775           LDX    #0
```

```
D6C6:BD 78 D6    776 ERSTR:   LDA  ERMES,X
D6C9:C9 2A       777          CMP  #'*'
D6CB:F0 07       778          BEQ  FIN1
D6CD:E8          779          INX
D6CE:20 7A E9    780          JSR  OUTPUT
D6D1:4C C6 D6    781          JMP  ERSTR
D6D4:20 A9 D6    782 FIN1:    JSR  WAIT1
D6D7:20 40 D6    783          JSR  ERASE
D6DA:4C 09 D0    784          JMP  TIMST
D6DD:45 4E 54    785 TIMSG:   ASC  'ENTER    TIME: '
D6E0:45 52 20
D6E3:54 49 4D
D6E6:45 3A 20
D6E9:78          786 COPY:    SEI
D6EA:AD 07 0F    787          LDA  CNT0
D6ED:8D 12 0F    788          STA  XCNT0
D6F0:AD 08 0F    789          LDA  CNT1
D6F3:8D 13 0F    790          STA  XCNT1
D6F6:AD 09 0F    791          LDA  CNT2
D6F9:8D 14 0F    792          STA  XCNT2
D6FC:AD 0A 0F    793          LDA  CNT3
D6FF:8D 15 0F    794          STA  XCNT3
D702:AD 0B 0F    795          LDA  CNT4
D705:8D 16 0F    796          STA  XCNT4
D708:AD 06 0F    797          LDA  SEC1
D70B:8D 11 0F    798          STA  XSEC1
D70E:AD 05 0F    799          LDA  SEC
D711:8D 10 0F    800          STA  XSEC
D714:AD 04 0F    801          LDA  MIN
D717:8D 0F 0F    802          STA  XMIN
D71A:AD 03 0F    803          LDA  HOUR
D71D:8D 0E 0F    804          STA  XHOUR
D720:AD 01 0F    805          LDA  MONTH
D723:8D 0C 0F    806          STA  XMONTH
D726:AD 02 0F    807          LDA  DAY
D729:8D 0D 0F    808          STA  XDAY
D72C:AD 00 0F    809          LDA  YEAR
D72F:8D 1C 0F    810          STA  XYEAR
D732:AD 23 0F    811          LDA  ZCNT0
D735:8D 1E 0F    812          STA  YCNT0
D738:AD 24 0F    813          LDA  ZCNT1
D73B:8D 1F 0F    814          STA  YCNT1
D73E:AD 25 0F    815          LDA  ZCNT2
D741:8D 20 0F    816          STA  YCNT2
D744:AD 26 0F    817          LDA  ZCNT3
D747:8D 21 0F    818          STA  YCNT3
D74A:58          819          CLI
D74B:60          820          RTS
D74C:52 45 54    821 MESS:    ASC  'RETURN   STARTS TIMER *'
D74F:55 52 4E
D752:20 53 54
D755:41 52 54
D758:53 20 54
D75B:49 4D 45
D75E:52 20 2A
D761:08          822 POUT:    PHP
D762:D8          823          CLD
D763:48          824          PHA
D764:4A         825          LSR  A
```

```
D765:4A              826        LSR   A
D766:4A              827        LSR   A
D767:4A              828        LSR   A
D768:18              829        CLC
D769:69 30           830        ADC   #48
D76B:20 00 F0        831        JSR   OUTPRI
D76E:68              832        PLA
D76F:C0 06           833        CPY   #6
D771:F0 08           834        BEQ   CONT
D773:29 0F           835        AND   #$0F
D775:18              836        CLC
D776:69 30           837        ADC   #48
D778:20 00 F0        838        JSR   OUTPRI
D77B:28              839 CONT:  PLP
D77C:60              840        RTS
D77D:A2 00           841 ADD1:  LDX   #0
D77F:20 C7 D3        842 ADD2:  JSR   INTX
D782:E8              843        INX
D783:E0 14           844        CPX   #20
D785:D0 F8           845        BNE   ADD2
D787:60              846        RTS
D788:AD 0C 0F        847 CHRMON: LDA  XMONTH
D78B:20 12 D6        848        JSR   DECONV
D78E:AA              849        TAX
D78F:CA              850        DEX
D790:A0 00           851        LDY   #0
D792:E0 00           852 MORE:  CPX   #0
D794:F0 06           853        BEQ   FOUND
D796:C8              854        INY
D797:C8              855        INY
D798:C8              856        INY
D799:CA              857        DEX
D79A:B0 F6           858        BCS   MORE
D79C:60              859 FOUND: RTS
```

.* SUCCESSFUL ASSEMBLY: NO ERRORS

| | | | |
|---|---|---|---|
| A00B ACR | D77D ADD1 | D77F ADD2 | D252 ALLOK |
| D657 BLANK | 0F19 CHAR1 | 0F1A CHAR2 | 0F1B CHAR3 |
| D788 CHRMON | D253 CLOCK | EB44 CLR | 0F07 CNT0 |
| 0F08 CNT1 | 0F09 CNT2 | 0F0A CNT3 | 0F0B CNT4 |
| D4E8 CNVT | D08F COLON | ?D0D2 COLON1 | D77B CONT |
| D6E9 COPY | ?EA13 CRLOW | D66C DATEST | 0F17 DATE |
| D12E DATST | 0F02 DAY | D4D0 DAYTAB | D612 DECONV |
| 0F29 DISBUF | D5B4 DISLOP | D5B2 DISOUT | D536 DISPLAY |
| D581 DODATE | D653 DONE | D138 DSTR | D146 DSTR2 |
| D640 ERASE | D678 ERMES | D6C1 ERROR | D692 ERRST |
| D68D ERR | D0F5 ER | D6C6 ERSTR | D266 EXIT |
| D6D4 FIN1 | D6A0 FIN | D79C FOUND | 0F1D GARB |
| 0F27 GARBX | D0A4 GOOD1 | D05B GOOD | D0E7 GOOD2 |
| 0F03 HOUR | A00E IER | ?A00D IFR | 0F28 INTFLG |
| D4CD INTRET | D3CD INT | D3C7 INTX | A400 IRQV1 |
| A401 IRQV2 | A480 KBPIAA | A482 KBPIAB | D631 LEATL |
| D62D LEAP | D628 LEAVE | D4DC LETCHK | D531 LFTOUT |
| D35A LF | D2E4 LOGN | D2DF LOGP | D2E6 LOG |
| D28F MAIN | D74C MESS | D099 MININ | D2BD MINUS |
| 0F04 MIN | D1C9 MOCHK | D19B MOIN | D4FB MONTAB |
| 0F01 MONTH | D792 MORE | D575 MOSP | D49A NEWMAN |
| D2A1 NOBRK | D150 NOTFIN | D08C NOTGOOD | D63D NO |
| D5C8 NOTIME | D4E6 NOTLET | D4F9 NOTNUM | D1E1 NOTR |
| D4EF NUMCHK | D51F NUMOUT | D223 OK10 | D15D OK1 |
| D23F OK11 | D172 OK2 | D18E OK3 | D1A3 OK4 |
| D1B1 OK5 | D1BF OK6 | D1F6 OK7 | D203 OK8 |

| | | | | | | |
|---|---|---|---|---|---|---|
| D20E | OK9 | D1F9 | OKAY | D541 | OKTIME | EF7B  OUTDD1 |
| F000 | OUTPRI | E97A | OUTPUT | EB9E | PHXY | A001  PTIA |
| ?D2B7 | PLUS | EBAC | PLXY | D761 | POUT | D392  FPRDAT |
| A411 | PRIFLG | D369 | PRINT | D258 | PROMPT | D2C0  Quiet |
| ?E93C | READ | FE96 | RED1 | D645 | REP | D63E  RET |
| 0F06 | SEC1 | D0DC | SECIN | 0F05 | SEC | D403  SKIP1 |
| D41A | SKIP2 | D438 | SKIP3 | D435 | SKIP4 | D42A  SKIP5 |
| D000 | START | D070 | STORE | D0B9 | STORMIN | D0F8  SloRSEC |
| A005 | T1H | A004 | T1L | D04E | TEST | D01C  TIMEO |
| 0F18 | TIME | ?D027 | TIMIN | D6DD | TIMSG | D009  TIMFT |
| D6AF | W1 | D6B6 | W2 | D6BB | W3 | D6C0  W4 |
| D009 | WAIT1 | 0F12 | XCNT0 | 0F13 | XCNT1 | 0F14  XCNT2 |
| 0F15 | XCNT3 | 0F16 | XCNT4 | 0F0D | XDAY | 0F0E  XHOUR |
| 0F0F | XMIN | 0F0C | XMONTH | 0F11 | XSEC1 | 0F10  XSECOND |
| 0F1C | XYEAR | 0F1E | YCNT0 | 0F1F | YCNT1 | 0F20  YCNT2 |
| 0F21 | YCNT3 | ?0F22 | YCNT4 | 0F00 | YEAR | D63A  YES |
| 0F23 | ZCNT0 | 0F24 | ZCNT1 | 0F25 | ZCNT2 | 0F26  ZCNT3 |

TABLE 7

SAMPLE NUMBER MLO-69-35 (Run 1)
OXYGEN ABSORPTION RATE (OXYGEN)

| | |
|---|---|
| Temperature, °C. (°F.) | 175 (347) |
| Oxygen Flow Rate, ml/min | 200 |
| Test Duration, hrs. | 4 |
| No metal catalyst | |
| Weight of Sample, grams | 20.03 |
| Weight of Condensate, grams | |
| Ambient Trap | 0.51 |
| Cold Trap | 0.91 |
| Induction period, minutes | 39.86 |
| Maximum Oxygen Absorption Rate micromoles/gram/min. | 12.195 |
| Elapsed Time at maximum rate, min. | 47.00 |
| Maximum Temperature attained by Sample, °C. (°F.) | 184.4 (364) |
| Increase, °C. (°F.) | 9.4 (17) |

TABLE 8

SAMPLE NUMBER MLO-69-35 (Run 1)
OXYGEN ABSORPTION - (CONTINUED)
Oxygen Absorption, Millimoles/gram

| Time, min. | Millimoles $O_2$ Absorbed/gram | Cumulative $O_2$ Absorbed, Millimoles/gram |
|---|---|---|
| 39.86 | 0.080 | 0.080 |
| 47.00 | 0.080 | 0.160 |
| 53.56 | 0.080 | 0.240 |
| 60.17 | 0.080 | 0.320 |
| 66.92 | 0.080 | 0.400 |
| 73.94 | 0.080 | 0.480 |
| 80.83 | 0.080 | 0.560 |
| 88.10 | 0.080 | 0.640 |
| 95.82 | 0.080 | 0.720 |
| 103.86 | 0.080 | 0.800 |
| 112.42 | 0.080 | 0.880 |
| 121.34 | 0.080 | 0.960 |
| 130.85 | 0.080 | 1.040 |
| 140.87 | 0.080 | 1.120 |
| 151.39 | 0.080 | 1.200 |
| 162.62 | 0.080 | 1.280 |
| 174.63 | 0.080 | 1.360 |
| 187.17 | 0.080 | 1.440 |
| 200.19 | 0.080 | 1.520 |
| 213.46 | 0.080 | 1.600 |
| 227.42 | 0.080 | 1.680 |

TABLE 9

SAMPLE NUMBER MLO-69-35 (Run 1)
OXYGEN ABSORPTION - (CONTINUED)
Oxygen Absorption Rate, Micromoles/Gram/Min

| Time, Min | $O_2$ Absorption Rate Micromoles/Gram/Min. | Interval Duration Min. | Time of Interval Midpoint, Min. |
|---|---|---|---|
| 0 | | | |
| | 2.007 | 39.86 | 19.93 |
| 39.86 | | | |
| | 11.204 | 7.14 | 43.43 |
| 47.00 | | | |
| | 12.195 | 6.56 | 50.28 |
| 53.56 | | | |
| | 12.102 | 6.61 | 56.86 |
| 60.17 | | | |
| | 11.851 | 6.75 | 63.54 |
| 66.92 | | | |
| | 11.396 | 7.02 | 70.43 |
| 73.94 | | | |
| | 11.611 | 6.89 | 77.38 |
| 80.83 | | | |
| | 11.004 | 7.27 | 84.46 |
| 88.10 | | | |
| | 10.362 | 7.72 | 91.96 |
| 95.82 | | | |
| | 9.950 | 8.04 | 99.84 |
| 103.86 | | | |
| | 9.345 | 8.56 | 108.14 |
| 112.42 | | | |
| | 8.968 | 8.92 | 116.88 |
| 121.34 | | | |
| | 8.412 | 9.51 | 126.09 |
| 130.85 | | | |
| | 7.984 | 10.02 | 135.86 |
| 140.87 | | | |
| | 7.604 | 10.52 | 146.13 |
| 151.39 | | | |
| | 7.123 | 11.23 | 157.01 |
| 162.62 | | | |
| | 6.661 | 12.01 | 168.62 |
| 174.63 | | | |
| | 6.379 | 12.54 | 180.90 |
| 187.17 | | | |
| | 6.144 | 13.02 | 193.68 |
| 200.19 | | | |
| | 6.028 | 13.27 | 206.83 |
| 213.46 | | | |
| | 5.730 | 13.96 | 220.44 |
| 227.42 | | | |

TABLE 10

SAMPLE NUMBER MLO-82-392 (Run 1)
OXYGEN ABSORPTION RATE-FROM AIR

| | |
|---|---|
| Temperature, °C. (°F.) | 200 (392) |
| Oxygen Flow Rate, ml/min | 200 |
| Test Duration, hrs. | 100 |
| No metal catalyst | |
| Weight of Sample, grams | 20.62 |
| Weight of Condensate, grams | |
| Ambient Trap | 0.06 |
| Cold Trap | 0.20 |
| Induction period, minutes (hrs) | 1903.78 (31.73) |
| Maximum Oxygen Absorption Rate micromoles/gram/min. | 5.900 |
| Elapsed Time at maximum rate, min. (hrs.) | 4439.63 (73.99) |
| Maximum Temperature attained | |
| by Sample, °C. (°F.) | 201.5 (395) |
| Increase, °C. (°F.) | 1.5 (3) |

TABLE 11

SAMPLE NUMBER MLO-82-392 (Run 1)
OXYGEN ABSORPTION - (CONTINUED)
Oxygen Absorption, Millimoles/gram

| Time, min. (hours) | Millimoles O$_2$ Absorbed/gram | Cumulative O$_2$ Absorbed, Millimoles/gram |
|---|---|---|
| 1903.78 (31.73) | 0.078 | 0.078 |
| 4068.91 (67.82) | 0.078 | 0.156 |
| 4439.63 (73.99) | 0.078 | 0.234 |
| 4452.85 (74.21) | 0.078 | 0.312 |
| 4469.96 (74.50) | 0.078 | 0.390 |
| 4492.85 (74.88) | 0.078 | 0.468 |
| 4527.50 (75.46) | 0.078 | 0.546 |
| 4592.92 (76.55) | 0.078 | 0.624 |
| 4802.80 (80.05) | 0.078 | 0.702 |
| 5602.76 (93.38) | 0.078 | 0.780 |

TABLE 12

SAMPLE NUMBER MLO-82-392 (Run 1)
OXYGEN ABSORPTION - (CONTINUED)
Oxygen Absorption Rate, Micromoles/Gram/Min

| Time, Min. (Hours) | O$_2$ Absorption Rate Micromoles/Gram/Min. | Interval Duration Min. (hrs.) | Time of Interval Midpoint, Hours |
|---|---|---|---|
| 0 | | | |
| | 0.041 | 1903.78 (31.73) | 15.87 |
| 1903.78 (31.73) | | | |
| | 0.036 | 2165.13 (36.09) | 49.78 |
| 4068.91 (67.82) | | | |
| | 0.210 | 370.72 (6.18) | 70.91 |
| 4439.63 (73.99) | | | |
| | 5.900 | 13.22 (0.22) | 74.10 |
| 4452.85 (74.21) | | | |
| | 4.559 | 17.11 (0.29) | 74.36 |
| 4469.96 (74.50) | | | |
| | 3.408 | 22.89 (0.38) | 74.69 |
| 4492.85 (74.88) | | | |
| | 2.251 | 34.65 (0.58) | 75.17 |
| 4527.50 (75.46) | | | |
| | 1.192 | 65.42 (1.09) | 76.01 |
| 4592.92 (76.55) | | | |
| | 0.372 | 209.88 (3.50) | 78.30 |
| 4802.80 (80.05) | | | |
| | 0.098 | 799.96 (13.33) | 86.72 |
| 5602.76 (93.38) | | | |

Clearly, many modifications and variations of the present invention are possible in light of the above teachings and it is therefore understood, that within the inventive scope of the inventive concept, the invention may be practiced otherwise than specifically claimed.

What is claimed is:

1. A system for automatic gas measuring, said system comprising:

means defining a controllable source of pressurized gas (200);

a controllable means for relieving excess pressure by venting said system (30), said controllable means connected by fluid conducting means to said means defining a controllable source of pressurized gas;

means for indicating incremental gas volume changes (202), said means for indicating having a first means defining a first container having a fixed volume space therein defined as a first volume (32) and a second means defining a second container having a fixed volume space therein defined as a second volume (34), said containers connected in series by fluid conducting means, said means for indicating having a liquid fluid flowing therethrough in response to pressure from said system;

said means for indicating being in fluid communication with said controllable source of pressurized gas (200) and said controllable means for relieving excess pressure by venting (30);

means for defining a liquid fluid movement indicating means (36, 38, 42, and 44) for monitoring a liquid fluid level, said liquid fluid movement indicating means being in said means for indicating incremental gas volume changes, said fluid movement indicating means responding to a first fluid level below said first container, responding to a second fluid level between said first and said second conrtainer, and responding to a third fluid level above said second container;

a gas reservoir (46);

means (206) for controlling said gas reservoir (46), said means for controlling said gas reservoir being in fluid communication with said gas reservoir (46), said controllable source of pressurized gas (200), said controllable means for relieving (30) and said means for indicating (202);

a means for actuating (204) for allowing the flow of, after a first or a second predetermined pressure condition, gas from said first and said second containers;

an initialization pressure means (208) for initially moving a liquid fluid level to set up an equilibrium pressure in said means for indicating incremental gas volume changes, said initialization pressure means being in fluid communication with said means for indicating said controllable source of pressurized gas, said controllable means for relieving excess pressure, and said means for controlling a gas reservoir;

means for circulating a gas through a liquid test sample for testing, said means for circulating being fluidly connected to said means for controlling a gas reservoir, said liquid test sample changing the pressure of said gas circulating; said means (204) for actuating said controllable source of pressurized gas, said controllable means for relieving excess pressure, said means for indicating incremental gas volume changes, and said means for controlling said gas reservoir; said means for actuating outputting a plurality of signals, one of said signals being indicative of either a gas volume intake of said first volume or a gas volume exhaust of said second volume;

said means for circulating a gas through a liquid test sample for testing including:

means for defining a sample test chamber for holding said liquid test sample therein; and means for circulating said gas through said sample test chamber; and means for recording (88) said plurality of signals.

2. A system as defined in claim 1 wherein said means defining controllable source of pressurized gas includes:
a source of pressurized gas;
a pressure regulator, said regulator connected to said source of pressurized gas and having thereon a low pressure delivery valve;
a surge space, said surge space connected to said pressure regulator;
a solenoid valve, said solenoid valve connected to said surge space and said means for actuating said solenoid valve being in a normally closed condition, said solenoid valve being activated to an open condition upon said liquid fluid contacting said third fluid level in said fluid movement indicating means whereby an incremental volume of said pressurized gas is input, said solenoid valve closing when said liquid fluid passes below said second fluid level.

3. A system as defined in claim 2 wherein said controllable means for relieving excess pressure therein comprises a solenoid valve in a normally closed condition, said solenoid valve being activated to an open condition upon said liquid fluid passing below said first level in said fluid movement indicating means whereby an incremental volume of gas is output from said system, said solenoid valve closing when said fluid level contacts said second fluid level in said fluid movement indicating means.

4. A system as defined in claim 3 wherein said initialization pressure means for initially moving a liquid fluid level to set up said equilibrium pressure comprises:
a gas buret having a valve thereon, said valve being openable to an ambient atmosphere and to said controllable means for venting said controllable source of pressurized gas and said means for controlling said gas reservoir,
a manometer connected to a bottom of said gas buret,
a leveling bulb connected to said manometer, and
said liquid fluid movement indicating means including four electrical contacts, said contacts being positioned in said fluid conducting means being tubes, a first electrical contact being an electrical common, a second electrical contact positioned to correspond with said first fluid level, a third electrical contact positioned to correspond to said second fluid level, and a fourth electrical contact positioned to correspond to said third fluid level.

5. A system as defined in claim 4 wherein said means for controlling said gas reservoir comprises:
a first solenoid valve being normally open, said first solenoid valve connected by tubes to said controllable source of pressurized gas, to said controllable means for relieving excess pressure, to said means for indicating incremental gas volume changes, to said means for initially moving and to said means for actuating;
said gas reservoir, said gas reservoir connected to said first solenoid valve; and
a second solenoid valve, said second solenoid valve connected by tubes to said gas reservoir, to said means for circulating a gas through a liquid test sample for testing, and to said means for actuating.

6. A system as defined in claim 5 wherein said means for actuating comprises:
a first controller (84), said first controller having input a first line (44) with said first electrical contact thereon, a second line (23) with a movable contact thereon and a power source line; said first controller outputting current through a relay coil circuit (104);
a second controller (86), said second controller having input said first line with said first electrical contact thereon, a second line (42) with said fourth electrical contact thereon and a movable contact (132) thereon, and a power source line; said second controller outputting current through a relay coil circuit (106);
a first relay means (74) being four-pole, double throw relay, a first section (108) thereof having a movable contact, a lower normally closed contact, and an upper normally open contact, said upper contact connected to said second contact of said means for indicating, said movable contact connected to said second contact of said means for indicating, said movable contact connected to said second line of said first controller, and said lower contact connected to said third electrical contact of said means for indicating; a second section (110) thereof having a movable contact, a lower contact, and an upper contact, said movable contact connected to a first terminal of a direct current (dc) source, and said lower contact connected to said solenoid (30) of said means for relieving excess pressure, said solenoid having a line connected to a second terminal of said direct current source whereby when said movable contact contacts said lower contact, said means for relieving allows gas to vent; a third section (112) thereof having a movable contact, a lower contact and an upper contact, said movable contact connected to a first terminal of said dc source; and a fourth section (114) thereof having a movable contact, an upper contact and a lower contact, said movable contact connected to said means for recording (A), said upper contact having thereon a positive voltage, said lower contact having thereon a negative voltage;
a second relay means (76) being a four-pole, double throw relay, said second relay being activated by said second controller (86) with current through said relay coil (106) of said second relay, a first section (132) thereof having a movable contact, an upper contact and a lower contact, said movable contact connected to said second line of said second controller, said upper contact connected to said electrical contact of means for indicating; a second section (134) having a movable contact, an upper contact, and a lower contact, said movable contact connected to said first terminal of said dc source, and said upper contact connected to said solenoid valve (20) of said source for pressur[e]ized gas, said solenoid valve connected to said second terminal of said dc source; a third section (136) thereto having a movable contact, an upper contact, and a lower contact, said movable contact connected to said first solenoid valve of said means for controlling a gas reservoir, said first solenoid valve further connected to said second terminal of said dc source, said upper contact connected to said solenoid valve of said source of pressurized gas, said lower contact connected to said lower contact of said third section of said first relay; and a fourth section (138) thereof having a movable contact, an upper contact, and a lower contact, said movable contact connected to said means for recording, said upper contact connected to said negative voltage, and said lower contact connected to said positive voltage;

a third relay (78), said relay being a single pole, single throw relay, said third relay having an actuator coil therein, said actuator coil being connected to said movable contact of said third section (136) of said second relay (76) and to a second terminal of said dc power source, said third relay having an upper contact and a lower contact;

a fourth relay (80) being a time delay relay upon breaking, said fourth relay being connected to said upper and said lower contacts of said third relay, (78) said fourth relay connected to said first terminal of said dc source and to said second solenoid valve of said means of controlling a gas reservoir, said second solenoid valve connected to said second terminal of said dc power source, upon activation of said third relay, activation of said second solenoid valve of said means for controlling a gas reeservoir is delayed a fixed period of time if a gas pressure in said means for indicating incremental gas volume changes remains about said equilibrium pressure for a period greater than said fixed period;

said dc source (92) of voltage, said source having said first and said second terminals thereon;

a voltage divider (94) connected to said dc source, said divider outputting said positive and said negative voltage to said first and said second relay; and a liquid fluid moving in said means for indicating incremental gas volume changes, said liquid fluid being electrically conductive and making contact with said first, second, third and fourth electrical contacts for completing electrical circuits.

* * * * *